United States Patent
Lohray et al.

(12)

(10) Patent No.: US 6,331,627 B1
(45) Date of Patent: Dec. 18, 2001

(54) INTERMEDIATES OF BENZOXAZINONE DERIVATIVES AND PREPARATION THEREOF

(75) Inventors: Vidya Bhushan Lohray; Braj Bhushan Lohray; Rao Bheema Paraselli; Rajagopalan Ramanujam; Ranjan Chakrabarti, all of Hyderabad (IN)

(73) Assignee: Reddy's Laboratories Ltd. (IN)

( * ) Notice: Subject to any disclaimer, the term of this patent is extended or adjusted under 35 U.S.C. 154(b) by 0 days.

(21) Appl. No.: 09/610,623

(22) Filed: Jul. 5, 2000

Related U.S. Application Data

(62) Division of application No. 09/179,141, filed on Oct. 26, 1998, now Pat. No. 6,130,214.

(30) Foreign Application Priority Data

Oct. 27, 1997 (IN) .......................................... 2419/MAS/97

(51) Int. Cl.[7] ...................... C07D 279/16; C07D 401/00; C07D 239/72; C07C 321/00; C07C 229/00
(52) U.S. Cl. .............................. 544/284; 544/50; 544/92; 544/287; 549/15; 549/365; 560/16; 560/35; 560/39; 562/426; 562/444
(58) Field of Search ................................ 544/50, 92, 284, 544/287; 549/15, 365; 560/35, 39, 16; 562/426, 444

(56) References Cited

U.S. PATENT DOCUMENTS

| 3,491,092 | 1/1970 | Grigat et al. ........................ 260/244 |
| 5,104,888 | 4/1992 | Yoshioka ............................... 514/369 |
| 5,306,726 | 4/1994 | Hulin ................................... 514/375 |

FOREIGN PATENT DOCUMENTS

| 0441539 | 8/1991 | (EP) . |
| 0903343 | 9/1998 | (EP) . |
| 9119702 | 12/1991 | (WO) . |
| 9401420 | 1/1994 | (WO) . |
| 9413650 | 6/1994 | (WO) . |
| 9517394 | 6/1995 | (WO) . |
| 9604260 | 2/1996 | (WO) . |
| 9725042 | 7/1997 | (WO) . |
| 9741097 | 11/1997 | (WO) . |

OTHER PUBLICATIONS

Buckle, D.S. "Non–Thiazolidnedione Antihyperglyceaemic Agents..." Bioorganic & Medicinal Chemistry Letters, vol. 6 No. 17 pp. 2121–2126, 1996.
Hulin, B. "Hypoglycemic Activity of A Series of ..." J. Med. Chem. 36, 1996, pp. 3897–3907.
Patent Abstracts of Japan vol. 97, No. 5, May 30, 1997 & JP 09 012575, Jan. 14, 1997.

*Primary Examiner*—Richard L. Raymond
*Assistant Examiner*—Tamthom N. Truong
(74) *Attorney, Agent, or Firm*—Ladas and Parry

(57) ABSTRACT

The present invention relates to novel antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereo-somers, their polymorphs, their pharmaceutically acceptable salts, their pharmaceutically acceptable solvates and pharmaceutically acceptable compositions containing them.

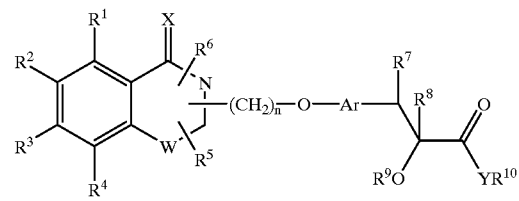

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates, novel intermediates and pharmaceutical compositions containing them.

6 Claims, No Drawings

INTERMEDIATES OF BENZOXAZINONE DERIVATIVES AND PREPARATION THEREOF

This is a divisional application of 9/179,141, filed Oct. 26, 1998, now U.S. Pat. No. 6,130,214.

FIELD OF INVENTION

The present invention relates to novel antiobesity and hypocholesterolermic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted aylcarboxylic acids of the general formula (I), their derivatives, their analogs, their tautomeric forms, their stereo-Somers, their polymorphs, their pharmaceutically acceptable salts, their pharmaceutically acceptable solvates and pharmaceutically acceptable compositions containing them.

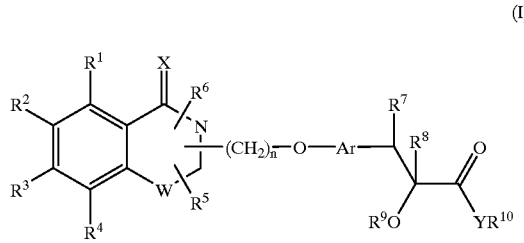

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates, novel intermediates and pharmaceutical compositions containing them.

The compounds of the present invention lower total cholesterol (TC); increase high density lipoprotein (HDL) and decrease low density lipoprotein (LDL), which have beneficial effect on coronary heart disease and atherosclerosis.

The compounds of general formula (I) are useful in reducing body weight and for the treatment and/or prophylaxis of diseases such as hypertension, coronary heart disease, atherosclerosis, stroke, peripheral vascular diseases and related disorders. These compounds are useful for the treatment of familial hypercholesterolemia, hypertiglyceridemia, lowering of atherogenic lipoproteins, very low density lipoprotein (VLDL) and LDL. The compounds of the present invention can be used for the treatment of certain renal diseases including glomerulonephritis, glomerulosclerosis, nephrotic syndrome, hypertensive nephrosclerosis, retinopathy, and nephropathy The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, xanthoma and for the treatment of cancer. The compounds of the present invention are useful in the treatment and/or prophylaxis of the above said diseases in combination/concomittant with one or more HMG CoA reductase inhibitors or hypolipidemic/hypolipoproteinemic agents such as fibric acid derivatives, nicotinic acid, cholestymmine, colestipol, probucol.

BACKGROUND OF INVENTION

Atherosclerosis and other peripheral vascular diseases are the major causes effect the quality of life of millions of people. Therefore, considerable attention has been directed towards understanding the etiology of hypercholesterolemia and hyperlipidemia and the development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as low density lipoprotein (LDL), intermediate density lipoprotein (IDL), high density lipoprotein (HDL) and partially as very low density lipoprotein (VLDL). Studies clearly indicate that there is an inverse correlationship between CAD and atherosclerosis with serum HDL-cholesterol concentrations. (Stampfer et al., *N. Engl. J. Med.*, 325 (1991), 373–381) and the risk of CAD increases with increasing levels of LDL and VLDL.

In CAD, generally "fatty streaks" in carotid, coronary and cerebral arteries, are found which are primarily free and esterified cholesterol. Miller et al, (*Br. Med J.*, 282 (1981), 1741–1744) have shown that increase in HDL-particles may decrease the number of sites of stenosis in coronary arteries of humans, and high level of HDL-cholesterol may protect against the progression of atherosclerosis. Picardo et aL, (*Arteriosclerosis* 6 (1986) 434–441) have shown by in vitro experiment that HDL is capable of removing cholesterol from cells. They suggest that HDL may deplete tissues of excess free cholesterol and transfer them to the liver (Macikinnon et al., *J. Biol Chem.* 261(1986), 2548–2552). Therefore, agents that increase HDL cholesterol would have therapeutic significance for the treatment of hypercholesterolernia and coronary heart diseases (CHD).

Obesity is a disease highly prevalent in affluent societies and in the developing world and which is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression has been a part of obesity treatment. There is a need for efficient therapy to fight this disease since it may lead to coronary heart idisease, diabetes, stroke, hyperlipidemia, gout, osteoarthritis, reduced fertility and many other psychological and social problems.

Diabetes and insulin resistance is yet another disease which severely effects the quality of life of a large population in the world. In insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperisulinemia have a contributory role in obesity, hypertension, atherosclerosis and type 2 diabetes melritus. The association of insulin resistance with obesity, hypertension and angina has been described as a syndrome having insulin resistance as the central pathogenic link-Syndrome-X.

Hyperlipidemia is the primary cause of cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ) isoform of PPAR (PPARγ) has been implicated in regulating differentiation of adipocytes (Endocrinology, (1994) 135: 798–800) and energy homeostasis (Cell, (1995) 83: 803–812), whereas the alpha (α) isoform of PPAR (PPARα) mediates fatty acid oxidation (Trend. Endocrin. Metab., (1993) 4: 291–296) thereby resulting in reduction of circulating free fatty acid in plasma (Current Biol. (1995) 5: 618–621). PPARα agonists have been found useful for the treatment of obesity (WO 97/36579). It has been recently disclosed that the hypolipidemic effect is enhanced when the molecule has both PPARα and PPARγ agonist activity and are suggested to be useful for the treatment of syndrome X (WO 97/25042). Synergism between the insulin sensitizer (PPARγ agonist) and HMG CoA reductase inhibitor has been observed which may be useful for the treatment of atherosclerosis and xanthoma. (EP 0 753 298).

It is known that PPARγ plays an important role in adipocyte differentiation (Cell, (1996) 87, 377–389). Ligand activation of PPAR is sufficient to cause complete terminal differentiation (Cell, (1994) 79, 1147–1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (Molecular Cell, (1998), 465–470; Carcinogenesis, (1998), 1949–53; Proc. Natl. Acad. Sci., (1997) 94, 237–241) and inhibition of cancer expression of prostate cancer tissue (Cancer Research (1998) 58, 3344–3352). This would be useful in the treatment of certain types of cancer, which expresses PPARγ and could leading to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (Proc. Natl. Acad. Sci., (1996) 93, 5793–5796) have reported that insulin sensitizers which perhaps due to their PPAR agonist expression and therefore lower plasm leptin concentrations. However, it has been recently disclosed that compounds having insulin sensitizing property also possess leptin sensitization activity. They lower the circulating plasma leptin concentrations by improving the target cell response to leptin (WO 98/02159).

A few β-aryl-α-hydroxy propionic acids, their derivatives, and their analogs have been reported to be useful in the treatment of hyperglycernia and hypercholesterolemia. Some of such compounds described in the prior art are outlined below:

i) U.S. Pat. No. 5,306,726; and WO 91/19702 disclose several 3-aryl-2-hydroxy-propionic acid derivatives of general formula (II a) and (II b) as hypolipidemic and hypoglycemic agents.

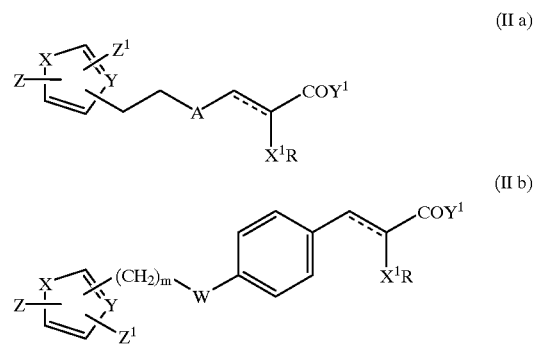

Examples of these compounds are shown in formula (II c) and (II d)

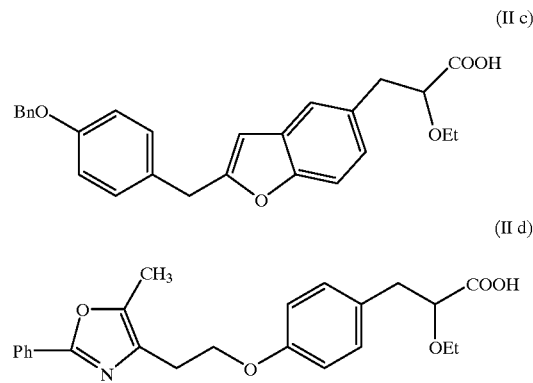

ii) International Patent Applications, WO 95/03038 and WO 96/04260 disclose compounds of formula (II e)

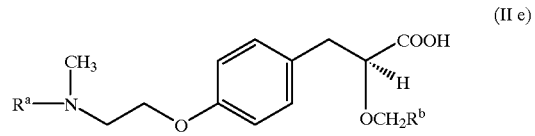

wherein $R^a$ represents 2-benzoxazolyl or 2-pyridyl and $R^b$ represents $CF_3$, $CH_2OCH_3$ or $CH_3$. A typical example is (S)-3-[4-[2-[N-(2-benzoxazolyl)-N-methylamino]ethoxy]phenyl]-2-(2,2,2-trifluoroethoxy)propanoic acid (II f).

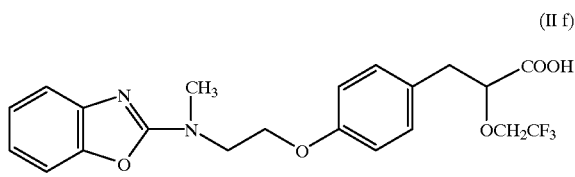

(II f)

iii) International Patent Application Nos. WO 94/13650, WO 94/01420 and WO 95/17394 disclose the compounds of general formula (II g)

$A^1$—X—$(CH_2)_n$—O—$A^2$—$A^3$—Y.$R^2$   (II g)

wherein $A^1$ represent aromatic heterocycle, $A^2$ represents substituted benzene ring and $A^3$ represents moiety of formula $(CH_2)_m$—CH—$(OR^1)$, wherein $R^1$ represents alkyl groups, m is an integer of the range of 1–5; X represents substituted or unsubstituted N; and Y represents C=O or C=S. $R^2$ represents $OR^3$ where $R^3$ may be hydrogen, alkyl, aralkyl, or aryl group; and n represents an integer in the range of 2–6. An example of these compounds is shown in formula (II h)

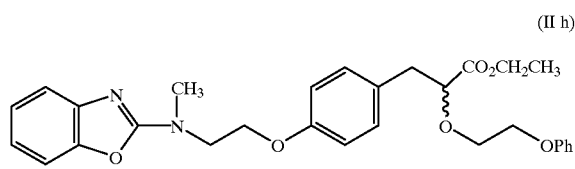

(II h)

SUMMARY OF THE INVENTION

With an objective to develop novel compounds for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetic complications thereof, for the treatment of diseases wherein insulin resistance is the pathophysiological mechanism, for the treatment and/or prophylaxis of leptin resistance and complications thereof, hypertension, atherosclerosis and coronary artery diseases with better efficacy, potency and lower toxicity, we focussed our research to develop new compounds effective in the treatment of above mentioned diseases. Effort in this direction has led to compounds having general formula (I).

The main objective of the present invention is therefore, to provide novel β-aryl-α-oxysubstituted alkycarboxylic acids, their derivatives, their analogs, their tautomeric forms, their stereoisomers, their polymorphs, their pharmaceutically acceptable salts, and their pharmaceutically acceptable solvates and pharmaceutical compositions containing them, or their mixtures.

Another objective of the present invention is to provide novel β-aryl-α-oxysubstituted alkylcarboxylic acids, their derivatives, their analogs, their tautomeric forms, their stereo-isomers, their polymorphs, their pharmaceutically acceptable salts, and their pharmaceutically acceptable solvates and pharmaceutical compositions containing them or their mixtures which may have agonist activity against PPARα and/or PPARγ, and or unsubstituted or substituted inhibit HMG CoA reductase, in addition to agonist activity against PPARα and/or PPARγ.

Another objective of the present invention is to provide novel β-aryl-α-oxysubstituted alkylcarboxylic acids, their derivatives, their analogs, their tautomeric forms, their stereo-isomers, their polymorphs, their pharmaceutically acceptable salts, and their pharmaceutically acceptable solvates and pharmaceutical compositions containing them or their mixtures having enhanced activities, without toxic effect or with reduced toxic effect.

Yet another objective of the present invention is to produce a process for the preparation of novel β-aryl-α-oxysubstituted alkylcarboxylic acids of the formula (I) as defined above, their derivatives, their analogs, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

Another objective of the present invention is to provide novel intermediates, a process for their preparation and use of the intermediates in processes for preparation of β-aryl-α-oxysubstituted alkyl carboxylic acids of formula (I), their derivatives, their analogs, their tautomers, their stereoisomers, their polymorphs, their salts and their pharmaceutically acceptable solvates.

DETAILED DESCRIPTION OF THE INVENTION

α-Oxysubstituted propionic acids, their derivatives, and their analogs of the present invention have the general formula (I)

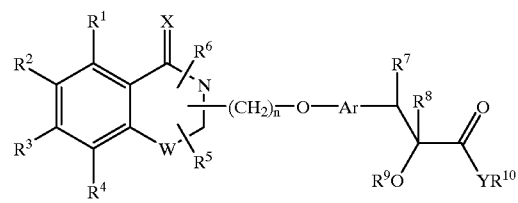

(I)

where X represents O or S; the groups $R^1$, $R^2$, $R^3$, $R^4$ and the groups $R^5$, and $R^6$ when attached to carbon atom may be the same or different and represent hydrogen, halogen, hydroxy, cyano, nitro, formyl; or unsubstituted or substituted groups selected from alkyl, cycloalkyl, alkoxy, cycloalkyloxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxy-carbonyl, aralkoxycarbonyl, amino, alkylamino which may be mono or dialkylamino group, arylamino, acylarnino, aralkylamino, aminoalkyl, hydroxyalkyl, alkoxyalkyl, aryloxyalkyl, aralkoxyalkyl, thioalkyl, alkylthio, alkoxycarbonylamino, aryloxycarbonylamino, aralkoxy-carbonylamino, carboxylic acid or its derivatives, or sulfonic acid or its derivatives; W represents O, S or a group $NR^{11}$; $R^{11}$ and the groups $R^5$, and $R^6$ when attached to nitrogen atom may be same or different and represent hydrogen, hydroxy, formyl or unsubstituted or substituted groups selected from alkyl, cycloalkyl, alkoxy, cycloalkoxy, aryl, aralkyl, aryloxy, aralkoxy, heterocyclyl, heteroaryl, heteroaryloxy, heteroaralkyl, heteroaralkoxy, acyl, acyloxy, hydroxyalkyl, amino, acylamino, alkylamino which may be mono or dialkylamino group, arylamino, aralkylamrino, aminoalkyl, alkoxycarbonyl, aryloxycarbonyl, aralkoxycarbonyl, alkoxyalkyl, aryloxyalyl, aralkoxyalkyl, alkylthio, thioalkyl, carboxylic acid derivatives, or sulfonic acid derivatives; n is an integer ranging from 1–4; Ar represents an unsubstituted or substituted divalent aromatic or heterocyclic group; $R^7$ represents hydrogen atom, hydroxy, alkoxy, halogen, lower alkyl, or unsubstituted or substituted aralkyl group or forms a bond with $R^8$; $R^8$ represents hydrogen atom, hydroxy, alkoxy, halogen, lower alkyl, acyl group, or unsubstituted or substituted aralkyl, or $R^8$ forms a bond together with $R^7$; $R^9$ may be hydrogen or unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminiocarbonyl, acyl, heterocyclyl, heteroaryl, or heteroaralkyl groups; $R^{10}$ may be hydrogen or unsubstituted or substituted groups selected from alkyl, cycloalkyl, aryl, aralkyl, heterocyclyl, heteroaryl, heteroaralkyl groups; Y represents oxygen or $NR^{12}$, where $R^{12}$ represents hydrogen, or unsubstituted or substituted alkyl, aryl, hydroxy alkyl, aralkyl, heterocyclyl, heteroaryl, or heteroaralkyi groups; $R^{10}$ and $R^{12}$ together may form a substituted or unsubstituted 5 or 6 membered cyclic structure containing carbon atoms, which may be unsubstituted or substituted contain one or more heteroatoms selected from oxygen, sulfuir or nitrogen; the linking group represented by —$(CH_2)_n$—O—may be attached either through nitrogen atom or carbon atom.

Suitable groups represented by $R^1$, $R^2$, $R^3$, $R^4$ and the groups, $R^5$, $R^6$ when attached to carbon atom may be selected from hydrogen, halogen atom such as fluozine, chlorine, bromine, or iodine; hydroxy, cyano, nitro, formyl; substituted or unsubstituted $(C_1-C_{12})$alkyl group, especially, linear or branched $(C_1-C_6)$alkyl group, such as methyl, ethyl, n-propyl, iso-propyl, n-butyl, iso-butyl, t-bulyl n-pentyl iso-pentyl hexyl and the like; cyclo$(C_3-C_6)$alkyl group such as cyclopropyl, cyclobutyl, cyclopentyl, cyclohexyl and the like, the cycloalkyl group may be substituted; cyclo$(C_3-C_6)$alkoxy group such as cyclopropyloxy, cyclobutyloxy, cyclopentyloxy, cyclohexyloxy and the like, the cycloalkoxy group may be substituted; aryl group such as phenyl or naphthyl, the aryl group may be substituted; aralkyl such as benzyl or phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heterocyclyl groups such as aziridinyl, pyrrolidinyl, morpholinyl, piperidinyl, piperazinyl and the like, the heterocyclyl group may be substituted; aralkoxy group such as benzyloxy, phenethyloxy, naphthyl-methyloxy, phenylpropyloxy and the like, the aralkoxy group may be substituted; hetero-arakyl group such as furanmethyl, pyridinemethyl, oxazolemethyl, oxazolemethyl and the like, the heteroaralkyl group may be substituted; aralkylamino group such as $C_6H_5CH_2NH$, $C_6H_5CH_2CH_2NH$, $C_6H_5CH_2NCH_3$ and the like, which may be substituted; alkoxycarbonyl such as methoxycarbonyl or ethoxycarbonyl which may be substituted; aryloxycarbonyl group such as or unsubstituted or substituted phenoxycarbonyl, naphthyloxycarbonyl and the like; aralkoxycarbonyl group such as benzyloxycarbonyl, phenethyloxycarbonyl, naphthyl-methoxycarbonyl and the like, which may be substituted; monoalkylamino group such as $NHCH_3$, $NHC_2H_5$, $NHC_3H_7$, $NHC_6H_{13}$ and the like, which may be substituted, dialkylamino group such as $N(CH_3)_2$, $NCH_3(C_2H_5)$, and the like, which may be substituted; alkoxyalkyl group such as methoxymethyl, ethoxymethyl, methoxyethyl, ethoxyethyl and the like which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; heteroar and heteroaralkoxy, wherein heteroaryl and heteroaralkyl moieties are as defined earlier and may be substituted; aryloxy group such as phenoxy, naphthyloxy, the aryloxy group may be substituted; arylamino group such as $HNC_6H_5$, $NCH_3(C_6H_5)$, $NHC_6H_4CH_3$, $NHC_6H_4$-Hal and the like, which may be substituted; amino group which may be substituted; amino $(C_1-C_6)$alkyl which may be substituted; hydroxy$(C_1-C_6)$ alkyl which may be substituted; $(C_1-C_6)$alkoxy such as methoxy, ethoxy, propyloxy, butyloxy, iso-propyloxy and the like which may be substituted; tbio$(C_1-C_6)$alkyl which may be substituted; $(C_1-C_6)$alkylthio which may be substituted; acyl group such as acetyl, propanoyl or benzoyl, the acyl group may be substituted; acylamino groups such as $NHCOCH_3$, $NHCOC_2H_5$, $NHCOC_3H_7$, $NHCOC_6H_5$ which may be substituted; aralkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4CH_3$, $NHCOOCH_2C_6H_4OCH_3$ and the like, which may be substituted; aryloxycarbonylamio group such as $NHCOOC_6H_5$, $NCH_3COOC_6H_5$, $NC_2H_5COOC_6H_5$, $NHCOOC_6H_4CH_3$, $NHCOOC_6H_4OCH_3$ and the like, which may be substituted; alkoxy-carbonylamino group such as $NHCOOC_2H_5$, $NHCOOCH_3$ and the like, which may be substituted; carboxylic acid or its derivatives such as amides, like $CONH_2$, CONHMe, $CONMe_2$, CONHEt, $CONEt_2$, CONHPh and the like, the carboxylic acid derivatives may be substituted; acyloxy group such as OCOMe, OCOEt, OCOPh and the like, which may be substituted; or sulfonic acid or its derivatives such as $SO_2NH_2$, $SO_2NHMe$, $SO_2NMe_2$, $SO_2NHCF_3$ and the like, the sulfonic acid derivatives may be substituted.

When the groups represented by $R^1$, $R^2$, $R^3$, $R^4$, $R^5$, and $R^6$ are substituted, the substituents may be selected from halogen, hydroxy, nitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkoxycarbonyl, alkylamino, alkoxyalkyl, alkylthio, thioalkyl groups, carboxylic acid or its derivatives, or sulfonic acid or its derivatives. The substituents are defined as above.

It is preferred that the substituents on $R^1$–$R^6$ represent halogen atom such as fluorine, chlorine, or bromine, hydroxy; or unsubstituted or substituted halogenated alkyl groups, the alkyl group is selected from a group such as methyl, ethyl, isopropyl, n-propyl, or n-butyl; cycloalkyl group such as cyclopropyl; aryl group such as phenyl; aralkyl group such as benzyl; $(C_1-C_3)$ alkoxy; beimyloxy, acyl or acyloxy groups;

Suitable $R^{11}$ and the groups $R^5$, $R^6$ when attached to nitrogen atom are selected from hydrogen, hydroxy, formyl;

substituted or unsubstituted $(C_1-C_{12})$alkyl group, especially, linear or branched $(C_1-C_6)$alkyl group, such as methyl, ethyl, n-propyl, iso-propyl, n-butyl, iso-butyl, t-butyl, n-pentyl, iso-pentyl, hexyl and the like; cyclo$(C_{3-6})$alkyl group such as cyclopropyl, cyclobutyl, cyclopentyl, cyclohexyl and the like, the cycloalkyl group may be substituted; cyclo$(C^3-C_6)$alkyloxy group such as cyclopropyloxy, cyclobutyloxy, cyclo-pentyloxy, cyclohexyloxy and the like, the cycloalkoxy group may be substituted; aryl group such as phenyl or naphthyl, the aryl group may be substituted; aralkyl such as benzyl or phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heterocyclyl groups such as aziridinyl, pyrrolidinyl, morpholinyl, piperidinyl, piperazinyl and the like, the heterocyclyl group may be substituted; aralkoxy group such as benzyloxy, phenethyloxy, naphthyl-methyloxy, phenylpropyloxy and the like, the aralkoxy group may be substituted; heteroaralkyl group such as furanmethyl, pyridinemethyl, oxazolemethyl, oxazolethyl and the like, the heteroaralkyl group may be substituted; aralkylamino group such as $C_6H_5CH_2NH$, $C_6H_5CH_2CH_2NH$, $C_6H_5CH_2NCH_3$ and the like, which may be substituted; alkoxycarbonyl such as methoxycarbonyl or ethoxycarbony which may be substituted; aryloxycarbonyl group such as unsubstituted or substituted phenoxycarbonyl, naphthyloxycarbonyl and the like; aralkoxycarbonyl group such as benzyloxycarbonyl, phenethyloxycarbonyl, naphthyl-methoxycarbonyl and the like, which may be substituted; monoalkylamino group such as $NHCH_3$, $NHC_2H_5$, $NHC_3H_7$, $NHC_6H_{13}$ and the like, which may be substituted; dialkylamino group such as $N(CH_3)_2$, $NCH_3(C_2H_5)$, and the like, which may be substituted; alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyl-oxymethyl and the like, which may be substituted; aralkoxyalkyl group such as $C_6H_5CH_2OCH_2$, $C_6H_5CH_2OCH_2CH_2$ and the like, which may be substituted; heteroaryloxy and heteroaralkoxy, wherein heteroaryl and heteroaralkyl moieties are as defined earlier and may be substituted; aryloxy group such as phenoxy, naphthyloxy, the aryloxy group may be substituted; arylamino group such as $NHC_6H_5$, $NCH_3(C_6H_5)$, $NHC_6H_4CH_3$, $NHC_6H_4$-Hal and the like, which may be substituted; amino group which may be substituted; amino $(C_1-C_6)$alkyl which may be substituted; hydroxy$(C_1-C_6)$ alkyl which may be substituted; $(C_1-C_6)$alkoxy such as methoxy, ethoxy, propyloxy, butyloxy, iso-propyloxy and the like which may be substituted; thio$(C_1-C_6)$alkyl which may be substituted; $(C_1-C_6)$alkylthio which may be substituted; acyl group such as acetyl, propanoyl or benzoyl, the acyl group may be substituted; acylamino groups such as $NHCOCH_3$, $NHCOC_2H_5$, $NHCOC_3H_7$, $NHCOC_6H_5$ which may be substituted; carboxylic acid derivatives such as amides, like $CONH_2$, $CONHMe$, $CONMe_2$, $CONHEt$, $CONEt_2$, $CONHPh$ and the like, the carboxylic acid derivatives may be substituted; acyloxy group such as $OCOMe$, $OCOEt$, $OCOPh$ and the like which may be unsubstituted or substituted; sulfonic acid derivatives such as $SO_2NH_2$, $SO_2NHMe$, $SO_2NMe_2$, $SO_2NHCF_3$ and the like, the sulfonic acid derivatives may be substituted.

When the groups represented by $R^{11}$ and the groups $R^5$, $R^6$ attached to nitrogen are substituted, preferred substituents may be selected from halogen such as fluorine, chlorine; hydroxy, acyl, acyloxy, or amino groups.

When the groups represented by $R^{11}$ and the groups $R^5$, $R^6$ are attached to nitrogen atom, $R^1-R^4$ are same as defined earlier.

The group represented by Ar includes substituted or unsubstituted groups selected from divalent phenylene, naphthylene, pyridyl, quinolinyl, benzofuryl, benzoxazolyl, benzo-thiazolyl, indolyl, indolinyl, azaindolyl, aindolinyl, indenyl, dihydrobenzofuryl, benzo-pyranyl, dihydrobenzopyranyl, pyrazolyl and the like. The substituents on the group represented by Ar include linear or branched or unsubstituted or substituted halogenated $(C_1-C_6)$alkyl, or unsubstituted or substituted halogenated $(C_1-C_3)$alkoxy, halogen, acyl, amino, acylamino, thio, carboxylic and sulfonic acids and their derivatives. The substituents are defined as they are for $R^1-R^4$.

It is more preferred that Ar represents a substituted or unsubstituted divalent, phenylene, naphthylene, benzofuryl, indolyl, indolinyl, quinolinyl, azaindolyl, azaindolinyl, benzothiazolyl or benzoxazolyl groups.

It is still more preferred that Ar is represented by divalent phenylene or naphthylene, which may be unsubstituted or substituted by methyl, halomethyl, methoxy or halomethoxy groups.

Suitable $R^7$ includes hydrogen, lower alkyl groups such as methyl, ethyl or propyl; hydroxy, $(C_1-C_3)$alkoxy; halogen atom such as fluorine, chlorine, bromine, or iodine; aralkyl such as benzyl, or phenethyl, which may be unsubstituted or substituted with halogen, hydroxy, $(C_1-C_3)$alkyl, $(C_1-C_3)$ alkoxy, benzyloxy, acetyl, acetyloxy groups, preferably with hydroxy, halogen, $(C_1-C_3)$alkyl or alkoxy $(C_1-C_3)$, or $R^7$ together with $R^8$ represent a bond.

Suitable $R^8$ may be hydrogen, lower alkyl groups such as methyl, ethyl or propyl; hydroxy, $(C_1-C_3)$alkoxy; halogen atom such as fluorine, chlorine, bromine, or iodine; acyl group such as linear or branched $(C_2-C_{10})$acyl group such as acetyl, propanoyl, butanoyl, pentanoyl, benzoyl and the like; aralkyl such as benzyl, phenethyl, which may be unsubstituted or substituted with halogen, hydroxy, $(C_1-C_3)$alkyl, $(C_1-C_3)$alkoxy, benzyloxy, acetyl, acetyloxy groups, preferably with hydroxy, halogen, $(C_1-C_3)$alkyl or $(C_1-C_3)$ alkoxy, or $R^8$ together with $R^7$ forms a bond.

It is preferred that $R^7$ and $R^8$ represent hydrogen atom or $R^7$ and $R^8$ together represent a bond.

Suitable groups represented by $R^9$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like, which may be substituted; $(C_3-C_7)$cycloalkyl group such as cyclopropyl, cyclobutyl, cyclopentyl, cyclohexyl, and the like, the cycloalkyl group may be substituted; aryl group such as phenyl, naphthyl, the aryl group may be substituted; heteroaryl group such as pyridyl, thienyl, furyl and the like, the heteroaryl group may be substituted; heteroaralkyl group such as furanmethyl, pyridinemethyl, oxazol-emethyl, oxazolthyl and the like, the heteroaralkyl group may be substituted; aralkyl group wherein the aryl group is as defined earlier and the alkyl moiety may contain $C_1-C_6$ atoms such as benzyl, phenethyl and the like, the aralkyl group may be substituted; heterocyclyl group such as aziridinyl, pyrrolidinyl, piperidinyl and the like, the heterocyclyl group may be substituted; $(C_1-C_6)$alkoxy$(C_1-C_6)$ alkyl group such as methoxymethyl, ethoxymethyl, methoxyethyl, ethoxypropyl and the like, the alkoxyalkyl group may be substituted; aryloxyalkyl group such as $C_6H_5OCH_2$, $C_6H_5OCH_2CH_2$, naphthyloxymethyl, naphthyl-oxyethyl and the like, which may be substituted; linear or branched $(C_2-C_{16})$acyl group such as acetyl, propanoyl, isopropanol, butanoyl, benzoyl, octanoyl, decanoyl and the like which may be substituted; $(C_1-C_6)$ alkoxycarbonyl, the alkyl group may be substituted; aryloxy-carbonyl such as phenoxycarbonyl, naphthyloxycarbonyl, the aryl group may be substituted; $(C_1-C_6)$alkylaminocarbonyl the alkyl group may be substituted; and arylaminocarbonyl such as PhNHCO, naphthylaminocarbonyl, the aryl moiety may be substituted. The substituents may be selected from halogen, hydroxy, formyl or nitro or unsubstituted or substituted groups selected from alkyl, cycloalkyl alkoxy, cycloalkoxy, aryl, aralkyl, aralkoxyalkyl, heterocyclyl, heteroaryl, heteroaralkyl, acyl, acyloxy, hydroxyalkyl, amino, acylamino, aryl-amino, aminoalkyl, aryloxy, alkoxycarbonyl, alkylamino, alkoxyalkyl, alkylthio, thioalkyl groups, carboxylic acid or its derivatives, or sulfonic acid or its derivatives. These groups are as defined above.

Suitable groups represented by $R^{10}$ may be selected from hydrogen, substituted or unsubstituted linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like; $(C_3-C_7)$cycloalkyl such as cyclopropyl, cyclopentyl, cyclohexyl and the like, the cycloalkyl group may be substituted; aryl group such as phenyl, naphthyl, the aryl group may be substituted; heteroaryl group such as pyridyl, thienyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group such as benzyl and phenethyl, the aralkyl group may be substituted; heterocyclyl group such as aziridinyl, pyrrolidinyl, piperidinyl and the like, the heterocyclyl group may be substituted. The substituents on $R^{10}$ may be selected from the same group of $R^1$–$R^4$ and are as defined above.

Suitable groups represented by $R^{12}$ may be selected from hydrogen, substituted or unsubstituted linear or branched $(C_1-C_{16})$alkyl, preferably $(C_1-C_{12})$alkyl; hydroxy $(C_1-C_6)$ alkyl which may be substituted; aryl group such as phenyl, naphthyl and the like, which may be substituted; aralkyl group such as benzyl and phenethyl and the like, which may be substituted; heterocyclyl group such as aziridinyl, pyrrolidinyl, piperidinyl, and the like which may be substituted; heteroaryl group such as pyridyl, thienyl, furyl and the like, which may be substituted; and heteroaralkyl group such as furanmethyl, pyridinemethyl, oxazolemethyl, oxazolethyl and the like, which may be substituted.

The cyclic structure formed by $R^{10}$ and $R^{12}$ may be a substituted or unsubstituted 5 or 6 membered cyclic structure containing carbon atoms which may be unsubstituted or substituted contains one or two heteroatoms selected from oxygen, nitrogen or sulfur.

Suitable ring structures formed by $R^{10}$ and $R^{12}$ together may be selected from pyrrolidinyl, piperidinyl, morpholinyl, piperazinyl, oxazolinyl, diazolinyl and the like.

Suitable substituents on the cyclic structure formed by $R^{10}$ and $R^{12}$ taken together may be selected from halogen, hydroxy, alkyl, oxo, aralkyl and the like.

Suitable n is an integer ranging from 1 to 4, preferably n represents an integer 1 or 2.

Pharmaceutically acceptable salts forming part of this invention include salts of the carboxylic acid moiety such as alkali metal salts like Li, Na, and K salts; alkaline earth metal salts like Ca and Mg salts; salts of organic bases such as lysine, arginine, guanidine, diethanolamine, choline, tromethamine and the like; ammonium or substituted ammonium salts, and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

Ethyl 2-ethoxy-3-[4-[2-[4-oxo-3,4-dihydro-1,3-benzoxazin-3-yl]ethoxy]phenyl]-2-propenoate;

(±)-Ethyl 2-ethoxy-3-[4-[2-[4-oxo-3,4-dihydro-1,3-benzoxazin-3-yl]ethoxy]phenyl]propanoate;

(+)-Ethyl 2-ethoxy-3-[4-[2-[4-oxo-3,4-dihydro-1,3-benzoxazin-3-yl]ethoxy]phenyl]propanoate;

(−)-Ethyl 2-ethoxy-3-[4-[2-[4-oxo-3,4-dihydro-1,3-benzoxazin-3-yl]ethoxy]phenyl]propanoate;

(±)-2-Ethoxy-3-[4-[2-[4-oxo-3,4-dihydro-1,3-benzoxazin-3-yl]ethoxy]phenyl]propanoic acid and its salts;

[2R, N(1S)]2-Ethoxy-3-[4-[2-[4-oxo-3,4-dihydro-1,3-benzoxazin-3-yl]ethoxy]phenyl]-N-(2-hydroxy-1-phenylethyl)propanamide;

[2S, N(1S)]2-Ethoxy-3-[4-[2-[4-oxo-3,4-dihydro-1,3-benzoxazin-3-yl]ethoxy]phenyl]-N-(2-hydroxy-1-phenylthyl)propanamide;

(+)-2-Ethoxy-3-[4-[2-[4-oxo-3,4-dihydro -1,3-benzoxazin-3-yl]ethoxy]phenyl]propanoic acid and its salts;

(−)-2-Ethoxy-3-[4-[2-[4-oxo-3,4-diydro-1,3-benzoxazin-3-yl]ethoxy]phenyl]propanoic acid and its salts;

(±)-Ethyl 2-phenoxy-3-[4-[2-[4-oxo-3,4-dihydro-1,3-benzoxazin-3-yl]ethoxy]phenyl]-2-propenoate;

(±)-Ethyl 2-ethoxy-3-[4-[2-[2,2-dimethyl-4-oxo-3,4-dihydro-1,3-benzoxazin-3-yl]ethoxy]phenyl] propanoate;

(+)-Ethyl 2-ethoxy-3-[4-[2-[2,2-dimethyl-4-oxo-3,4-dihydro-1,3-benzoxazin-3-yl]-ethoxy]phenyl] propanoate;

(−)-Ethyl 2-ethoxy-3-[4-[2-[2,2-dimethyl-4-oxo-3,4-dihydro-1,3-benzoxazin-3-yl]ethoxy]phenyl] propanoate;

(±)-2-Ethoxy-3-[4-[2-[2,2-dimethyl-4-oxo-3,4-dihydro-1,3-benzoxazin-3-yl]ethoxy]phenyl]propanoic acid and its salts;

(+)-2-Ethoxy-3-[4-[2-[2,2-dimethyl-4-oxo-3,4-dihydro-1,3-benzoxazin-3-yl]ethoxy]phenyl]propanoic acid and salts;

(−)-2-Ethoxy-3-[4-[2-[2,2-dimethyl-4-oxo-3,4-dihydro-1,3-benzoxazin-3-yl]ethoxy]phenyl]propanoic acid and its salts;

(±)-Methyl 2-ethoxy-3-[4-[[4-oxo-3,4-dihydro-1,3-benzoxazin-2-yl]methoxy]phenyl]propanoate;

(+)-Methyl 2-ethoxy-3-[4-[[4-oxo-3,4-dihydro-1,3-benzoxazin-2-yl]methoxy]phenyl]propanoate;

(−)-Methyl 2-ethoxy-3-[4-[[4-oxo-3,4-dihydro-1,3-benzoxazin-2-yl]methoxy]phenyl]propanoate;

(±)2-Ethoxy-3-[4-[[4-oxo-3,4-dihydro-1,3-benzoxazin-2-yl]methoxy]phenyl]propanoic acid and its salts;

(+)-2-Ethoxy-3-[4-[[4-oxo-3,4-dihydro-1,3-benzoxazin-2-yl]methoxy]phenyl]propanoic acid and its salts;

(−)-2-Ethoxy-3-[4-[[4-oxo-3,4-dihydro-1,3-benzoxazin-2-yl]methoxy]phenyl]propanoic acid and its salts;
(±)-Methyl 2-ethoxy-3-[4-[[4-oxo-1,2,3,4-tetrahydro-2-quinazolinyl]methoxy]phenyl]propanoate;
(+)-Methyl 2-ethoxy-3-[4-[[4-oxo-1,2,3,4-tetrahydro-2-quinazolinyl]methoxy]phenyl]propanoate;
(−)-Methyl 2-ethoxy-3-[4-[[4-oxo-1,2,3,4-tetrahydro-2-quinazolinyl]methoxyl]phenyl]propanoate;
(±)2-Ethoxy-3-[4-[[4-oxo-1,2,3,4-tethydro-2-quinazolinyl]methoxy]phenyl]propanoic acid;
(+)-2-Ethoxy-3-[4-[[4-oxo-1,2,3,4-tetrahydro-2-quinazolinyl]methoxy]phenyl]propanoic acid;
(−)-2-Ethoxy-3-[4-[[4-oxo-1,2,3,4-tetrahydro-2-quinazolinyl]methoxy]phenyl]propanoic acid;
(±)-Methyl 2-ethoxy-3-[4-[[6-chloro-4-oxo-1,2,3,4-tetrahydro-2-quinazolinyl]methoxy]phenyl]propanoate;
(+)-Methyl 2-ethoxy-3-[4-[[6-chloro-4-oxo-1,2,3,4-tetrahydro-2-quinazolinyl]methoxy]phenyl]propanoate;
(−)-Methyl 2-ethoxy-3-[4-[[6-chloro-4-oxo-1,2,3,4-tetrahydro-2-quinazolinyl]methoxylphenyl]propanoate;
(±)-2-Ethoxy-3-(4-[[6-chloro-4-oxo-1,2,3,4-tetrahydro-2-quinazolinyl]methoxy]phenyl]propanoic acid and its salts;
(±)-2-Ethoxy-3-[4-[[6-chloro-4-oxo-1,2,3,4-tetahydro-2-quinazolinyl]methoxy]phenyl]propanoic acid and its salts;
(−)-2-Ethoxy-3-[4-[[6-chloro-4-oxo-1,2,3,4-tetrahydro-2-quinazolinyl]methoxy]phenyl]propanoic acid and its salts;
(±)-Methyl 2-ethoxy-3-[4-[[3-methyl-4-oxo-1,2,3,4-tetrahydro -2-quinazolinyl]methoxy]phenyl]propanoate;
(+)-Methyl 2-ethoxy-3-[4-[[3-methyl-4-oxo-1,2,3,4-tetrahydro-2-quinazolinyl]methoxy]phenyl]propanoate;
(−)-Methyl 2-ethoxy-3-[4-[[3-methyl-4-oxo-1,2,3,4-tetrahydro-2-quinazolinyl]methoxy]phenyl]propanoate;
(+)-Methyl 2-ethoxy-3-[4-[[3-methyl-4-oxo-3,4-dihydro-1,3-benzoxazin-2-yl]methoxy]phenyl]propanoate;
(+)-Methyl 2-ethoxy-3-[4-[[3-methyl-4-oxo-3,4-dihydro-1,3-benzoxazin-2-yl]methoxy]phenyl]propanoate;
(−)-Methyl 2-ethoxy-3-[4-[[3-methyl-4-oxo-3,4-dihydro-1,3-benzoxazin-2-yl]methoxy]phenyl]propanoate;
(±)-2-Ethoxy-3-[4-[[3-methyl-4-oxo-3,4-dihydro-1,3-benzoxazin-2-yl]methoxy]phenyl]propanoic acid and its salts;
(+)-2-Ethoxy-3-[4-[[3-methyl-4-oxo-3,4-dihydro-1,3-benzoxazin-2-yl]methoxy]phenyl]propanoic acid and its salts;
(−)-2-Ethoxy-3-[4-[[3-methyl-4-oxo-3,4-dihydro-1,3-benzoxazin-2-yl]methoxy]phenyl]propanoic acid and its salts;
(±)-Methyl 2-ethoxy-3-[4-[[3-ethyl-4-oxo-1,2,3,4-tetrahydro-2-quinazolinyl]methoxy]phenyl]propanoate;
(+)-Methyl 2-ethoxy-3-[4-[[3-ethyl-4-oxo1,2,3,4-tetrahydro-2quiazolinyl]methoxy]phenyl]propanoate;
(+)-Methyl 2-ethoxy-3-[4-[[3-ethyl-4-oxo-1,2,3,4-tetrahydro-2-quinazolinyl]methoxy]phenyl]propanoate;
(±)-2-Ethoxy-3-[4-[[3-ethyl-4-oxo-1,2,3,4-tetrahydro-2-quinazolinyl]methoxy]phenyl]propanoic acid and its salts;
(+)-2-Ethoxy-3-[4-[[3-ethyl-4-oxo-1,2,3,4-tetrahydro-2-quinazolinyl]methoxy]phenyl]propanoic acid and its salts;
(−)-2-Ethoxy-3-[4-[[3-ethy-4-oxo-1,2,3,4-tetrahydro-2-quinazolinyl]methoxy]phenyl]propanoic acid and its salts;
(±)-Methyl-2-ethoxy-3-[4-[[1,3-dimethyl-4-oxo-1,2,3,4-tetrahydro-2-quinazolinyl]methoxy]phenyl]propanoate;
(+)-Methyl 2-ethoxy-3-[4-[[1,3-dimethyl-4-oxo-1,2,3,4-tetrahydro-2-quinazolinyl]methoxy]phenyl]propanoate;
(−)-Methyl 2-ethoxy-3-[4-[[1,3-dimethyl-4-oxo-1,2,3,4-tetrahydro-2-quinazolinyl]methoxy]phenyl]propanoate;
(±)-2-Ethoxy-3-[4-[[1,3-dimethyl-4-oxo-1,2,3,4-tetrahydro-2-quinazolinyl]methoxy]phenyl]propanoic acid and salts;
(+)-2-Ethoxy-3-[4-[[1,3-dimethyl-4-oxo-1,2,3,4-4-tetrahydro-2-quinazolinyl]methoxy]phenyl]propanoic acid and salts;
(−)-2-Ethoxy-3-[4-[[1,3-dimethyl-4-oxo-1,2,3,4-tetrahydro-2-quinazolinyl]methoxy]phenyl]propanoic acid and salts;
(±)-Methyl 2-phenoxy-3-[4-[[4-oxo-1,2,3,4-tetrahydro-2-quinazolinyl]methoxy]phenyl]propanoate;
(+)-Methyl 2-phenoxy-3-[4-[[4-oxo-1,2,3,4-tetrahydro-2-quinazolinyl]methoxy]phenyl]propanoate;
(−)-Methyl 2-phenoxy-3-[4-[[4-oxo-1,2,3,4-tetrahydro-2-quinazolinyl]methoxy]phenyl]propanoate;
(±)-2-Phenoxy-3-[4-[[4-1,2,3,4-tetrahydro-2-quinazolinyl]methoxy]phenyl]propanoic acid and its salts;
(+)-2-Phenoxy-3-[4-[[4-oxo-1,2,3,4-tetrahydro-2-quinazolinyl]methoxy]phenyl]propanoic acid and its salts;
(−)-2-Phenoxy-3-[4-[[4-oxo-1,2,3,4-tetrahydro-2-quinazolinyl]methoxy]phenyl]propanoic acid and its salts;
(±)-Methyl 2-phenoxy-3-[4-[[6-chloro-4-oxo-1,2,3,4-tetrahydro-2-quinazolinyl]methoxy]phenyl]propanoate;
(+)-Methyl 2-phenoxy-3-[4-[[6-chloro-4-oxo-1,2,3,4-tetrahydro-2-quinazolinyl]methoxy]phenyl]propanoate;
(−)-Methyl 2-phenoxy-3-[4-[[6-chloro-4-oxo-1,2,3,4-tetrahydro-2-quinazolinyl]methoxy]phenyl]propanoate;
(±)-2-Phenoxy-3-[4-[[6-chloro-4-oxo-1,2,3,4-tetrahydro-2-quinazolinyl]methoxy]phenyl]propanoic acid and its salts;
(+)-2-Phenoxy-3-[4-[[6-chloro-4-oxo-1,2,3,4-tetrahydro-2-quinazolinyl]methoxy]phenyl]propanoic acid and its salts;
(−)-2-Phenoxy-3-[4-[[6-chloro-4-oxo-1,2,3,4-tetrahydro-2-quinazolinyl]methoxy]phenyl]propanoic acid and its salts;
(±)-Ethyl 2-ethoxy-3-[4-[2-[6-nitro-4-oxo-3,4-dihydro-1,3-benzoxazin-3-yl]ethoxy]phenyl]propanoate;
(+)-Ethyl 2-ethoxy-3-[4-[2-[6-nitro-4-oxo-3,4-dihydro-1,3-benzoxazin-3-yl]ethoxy]phenyl]propanoate;

(−)-Ethyl 2-ethoxy-3-[4-[2-[6-nitro-4-oxo-3,4-dihydro-1,3-benzoxazin-3-yl]ethoxy]phenyl]propanoate;
(±)-2-Ethoxy-3-[4-[2-[6-nitro-4-oxo-3,4-dihydro-1,3-benzoxazin-3-yl]ethoxy]propanoic acid and its salts;
(+)-2-Ethoxy-3-[4-[2-[6-nitro-4-oxo-3,4-dihydro-1,3-benzoxazin-3-yl]ethoxy]propanoic acid and its salts;
(−)-2-Ethoxy-3-[4-[2-[6-nitro-4-oxo-3,4-dihydro-1,3-benzoxazin-3-yl]ethoxy]phenyl]propanoic acid and its salts;
(±)-Ethyl 2-ethoxy-3-[4-[2-[6-acetyl-4-oxo-3,4-dihydro-1,3-benzoxazin-3-yl]ethoxy]phenyl]propanoate;
(+)-Ethyl 2-ethoxy-3-[4-[2-[6-acetyl-4-oxo-3,4-dihydro-1,3-benzoxazin-3-yl]ethoxy]phenyl]propanoate,
(−)-Ethyl 2-ethoxy-3-[4-[2-[6-acetyl-4-oxo-3,4-dihydro-1,3-benzoxazin-3-yl]ethoxy]phenyl]propanoate;
(±)-2-ethoxy-3-[4-[2-[6-acetyl-4-oxo-3,4-dihydro-1,3-benzoxazin-3-yl]ethoxy]phenyl]propanoic acid and its salts;
(+)-2-Ethoxy-3-[4-[2-[6-acetyl-4-oxo-3,4-dihydro-1,3-benzoxazin-3-yl]ethoxy]phenyl]propanoic acid and its salts; and
(−)-2-Ethoxy-3-[4-[2-[6-acetyl-4-oxo-3,4-dihydro-1,3-benzoxazin-3-yl]ethoxy]phenyl]propanoic acid and its salts;

According to a feature of the present invention, the compound of formula (I) where $R^7$ and $R^8$ together represent a bond, Y represents oxygen atom, $R^1$, $R^2$, $R^3$, $R^4$, $R^5$, $R^6$, X, W, $R^9$, $R^{10}$, n and Ar are as defined earlier, may be prepared by any of the following routes shown in Scheme-I below Scheme-I

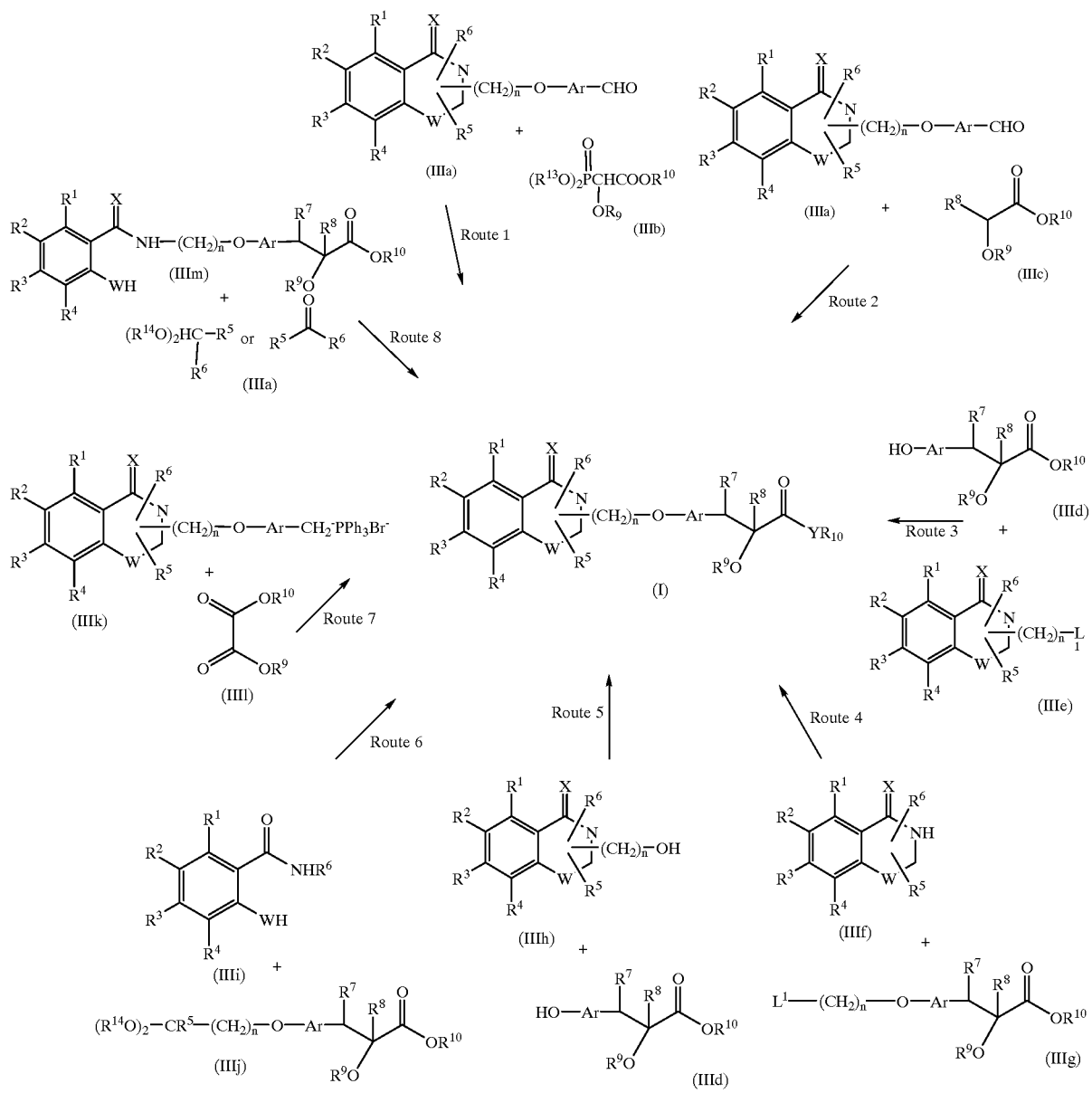

Route (1): The reaction of a compound of the general formula (IIIa) where all other symbols are as defined earlier, with a compound of formula (IIIb), where $R^9$, $R^{10}$ are as defined earlier excluding hydrogen atom and $R^{13}$ represents $(C_1-C_6)$alkyl group, to yield a compound of general formula (I) defined above may be carried out in the presence of a base such as alkali metal hydrides like NaH, KH or organolithiumns like $CH_3Li$, BuLi and the like or alkoxides such as NaOMe, NaOEt, $BuO^-K^+$ or mixtures thereof. The reaction may be carried out in the presence of solvents such as THF, dioxane, DMF, DMSO, DME and the like or mixtures thereof. HMPA may be used as cosolvent. The reaction temperature may range from −78° C. to 50° C., preferably at a temperature in the range of −10° C. to 30° C. The compound of general formula (IIIb) may be prepared by Arbuzov reaction.

The intermediate of formula (IIIa) wherein W represents nitrogen atom and the linker group $-(CH_2)_n-$ is attached through carbon atom and the process for its preparation have been disclosed in the Copending application Ser. No. 08/982,911.

Alternatively, the compound of formula (I) may be prepared by reacting the compound of formula (IIIa) where all symbols are as defined earlier with Wittig reagents such as $Hal^-Ph_3P^+CH-(OR^9)CO_2R^{10}$ under similar reaction conditions as described above.

Route (2): The reaction of a compound of the general formula (IIIa) where all other symbols are as defined earlier, with a compound of formula (IIIc) where $R^8$ represents a hydrogen atom and all other symbols are as defined above to produce a compound of formula (I) defined above may be carried out in the presence of a base. The nature of the base is not critical. Any base normally employed for aldol condensation reaction may be employed; bases like metal hydride such as NaH, or KH; metal alkoxides such as NaOMe, $K^+BuO^-$, or NaOEt; metal amides such as $LiNH_2$, or $LiN(iPr)_2$ may be used. Aprotic solvent such as THF, ether, or dioxane may be used. The reaction may be carried out in an inert atmosphere which may be maintained by using inert gases such as $N_2$, Ar, or He and the reaction is more effective under anhydrous conditions. Temperature in the range of −80° C. to 35° C. may be used. The β-hydroxy product initially produced may be dehydrated under conventional dehydration conditions such as treating with PTSA in solvents such as benzene or toluene. The nature of solvent and dehydrating agent is not critical. Temperature in the range of 20° C. to reflux temperature of the solvent used may be employed, preferably at reflux temperature of the solvent by continuous removal of water using a Dean Stark water separator.

Route (3): The reaction of compound of formula (IIIe) where all symbols are as defined earlier and $L^1$ represents a leaving group such as halogen atom, p-toluenesulfonate, methanesulfonate, trifluoromethanesulfonate and the like, with a compound of formula (IIId) where $R^7$ and $R^8$ together represent a bond, and all other symbols are as defined earlier to produce a compound of the formula (I) defined above may be carried out in the presence of aprotic solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 0° C.–120° C., preferably at a temperature in the range of 30° C.–100° C. The duration of the reaction may range from 1 to 24 hours, preferably from 2 to 12 hours. The compound of formula (IIId) can be prepared according to known procedure by a Wittig Horner reaction between the hydroxy protected aryl aldehyde such as benzyloxy aryl aldehyde and the compound of formula (IIIb), followed by deprotection.

Route (4): The reaction of a compound of general formula (IIIf) where all symbols are as defined earlier with a compound of general formula (IIIg) where $R^7$, $R^8$ together represent a bond, and all symbols are as defined earlier and $L^1$ is a leaving group such as halogen atom, p-toluenesulfonate, methanesulfonate, trifluoromethanesulfonate and the like, preferably a halogen atom to produce a compound of general formula (I) defined above where the linker group $-(CH_2)_n-O-$ is attached to nitrogen atom may be carried out in the presence of solvents such as DMSO, DMF, DME, THF, dioxane, ether and the like or a combination thereof. The reaction may be carried out in an inert atmosphere which may be maintained by using inert gases such as $N_2$, Ar, He. The reaction may be effected in the presence of a base such as alkis like sodium hydroxide or potassium hydroxide, alkali metal carbonates like sodium carbonate or potassium carbonate; alkali metal hydrides such as sodium hydride or potassium hydride; organometallic bases like n-butyl lithium, alkali metal amides like sodamide or mixtures thereof. The amount of base may range from 1 to 5 equivalents, based on the amount of the compound of formula (IIIf), preferably the amount of base ranges from 1 to 3 equivalents. Phase transfer catalysts such as tetraalkylammonium halide or hydroxide may be added. The reaction may be caried out at a temperature in the range of 0° C. to 150° C., preferably at a temperature in the range of 15° C. to 100° C. The duration of the reaction may range from 0.25 to 48 hours, preferably from 0.25 to 12 hours.

Route (5): The reaction of compound of general formula (IIIh) where all symbols are as defined earlier, with a compound of general formula (IIId) where $R^7$ and $R^8$ together represent a bond, and all other symbols are as defined earlier to produce a compound of formula (I) defined above may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route (6): The reaction of compound of general formula (IIIi) where all symbols are as defined earlier, with a compound of formula (IIIj) where $R^{14}$ represents lower alkyl group, $R^7$ and $R^8$ together represent a bond, and all other symbols are as defined earlier to produce a compound of formula (I) wherein the linker group —$(CH_2)_n$—O— is linked through carbon atom may be carried out in neat or in the presence of solvents such as THF, $CHCl_3$, benzene, toluene, hexane, dioxane and the like or mixture thereof. The reaction may be carried out at a temperature in the range of 0° C. to 250° C. preferably at a temperature in the range of 10° C. to 150° C. The reaction may be carried out in the presence of an acid or a base. The selection of acid or base is not critical. The examples of such acids include $H_2SO_4$, HCl, pTsOH, PPE (polyphosphoric ethyl ester) and the like. Examples of bases include pyrrolidine, lutidine, triethyl amine, diisopropylethyl amine, piperidine and the like. The reaction may be carried out in an inert atmosphere which may be maintained by using inert gases such as $N_2$, Ar or He. The duration of the reaction may range from 0.25 to 24 h preferably, from 1 to 12 h.

Route (7): The reaction of a compound of formula (IIIk) where all symbols are as defined earlier with a compound of formula (IIIl) where $R^9=R^{10}$ and are as defined earlier excluding hydrogen atom to produce a compound of the formula (I) where $R^7$ and $R^8$ together represent a bond may be carried out neat in the presence of a base such as alkali metal hydrides like NaH, or KH or organolithiums like $CH_3Li$, BuLi and the like or alkoxides such as NaOMe, NaOEt, $K^+BuO^-$ and the like or mixtures thereof. The reaction may be carried out in the presence of aprotic solvents such as THF, dioxane, DMF, DMSO, DME and the like or mixtures thereof. HMPA may be used as cosolvent. The reaction temperature may range from −78° C. to 100° C., preferably at a temperature in the range of −10° C. to 50° C.

Route (8): The reaction of compound of general formula (IIIm), where $R^7$ and $R^8$ together represent a bond and all other symbols are as defined earlier with a compound of general formula (IIIn) where $R^{14}$ represents lower alkyl group and where all symbols are as defined earlier to produce a compound of general formula (I), where —$(CH_2)_n$—O—linker group is attached through nitrogen atom and all other symbols are as defined earlier may be carried out in neat or in the presence of solvents such as xylene, toluene, THF, dioxane, acetic acid, DMF, DMSO and the like or mixtures thereof The reaction may be carried out in an inert atmosphere which may be maintained by using inert gases such as $N_2$, Ar or He. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Examples of such bases include organic bases such as pyridine, lutidine, triethyl amine, diisopropylethyl amine and the like, metal carbonates such as $K_2CO_3$, and $Na_2CO_3$. Examples of acids include organic acids such as AcOH, $C_2H_5COOH$ butyric acid, trifluoroacetic acid, p-toluenesulfonic acid, benzenesulfonic acid and the like, mineral acids such as HCl, HBr etc. The duration of the reaction may range from 0.25 to 48 hours, preferably from 0.50 to 18 hours.

In yet another embodiment of the present invention, the compound of general formula (I) where all symbols are as defined earlier, $R^7$ represents hydrogen atom, hydroxy, alkoxy, halogen, lower alkyl, or unsubstituted or substituted aralkyl group; $R^8$ represents hydrogen atomn, hydroxy, alkoxy, halogen, lower alkyl; or unsubstituted or substituted aralkyl or acyl group; and Y represents an oxygen atom can be prepared by one or more of the processes shown in Scheme-II below:

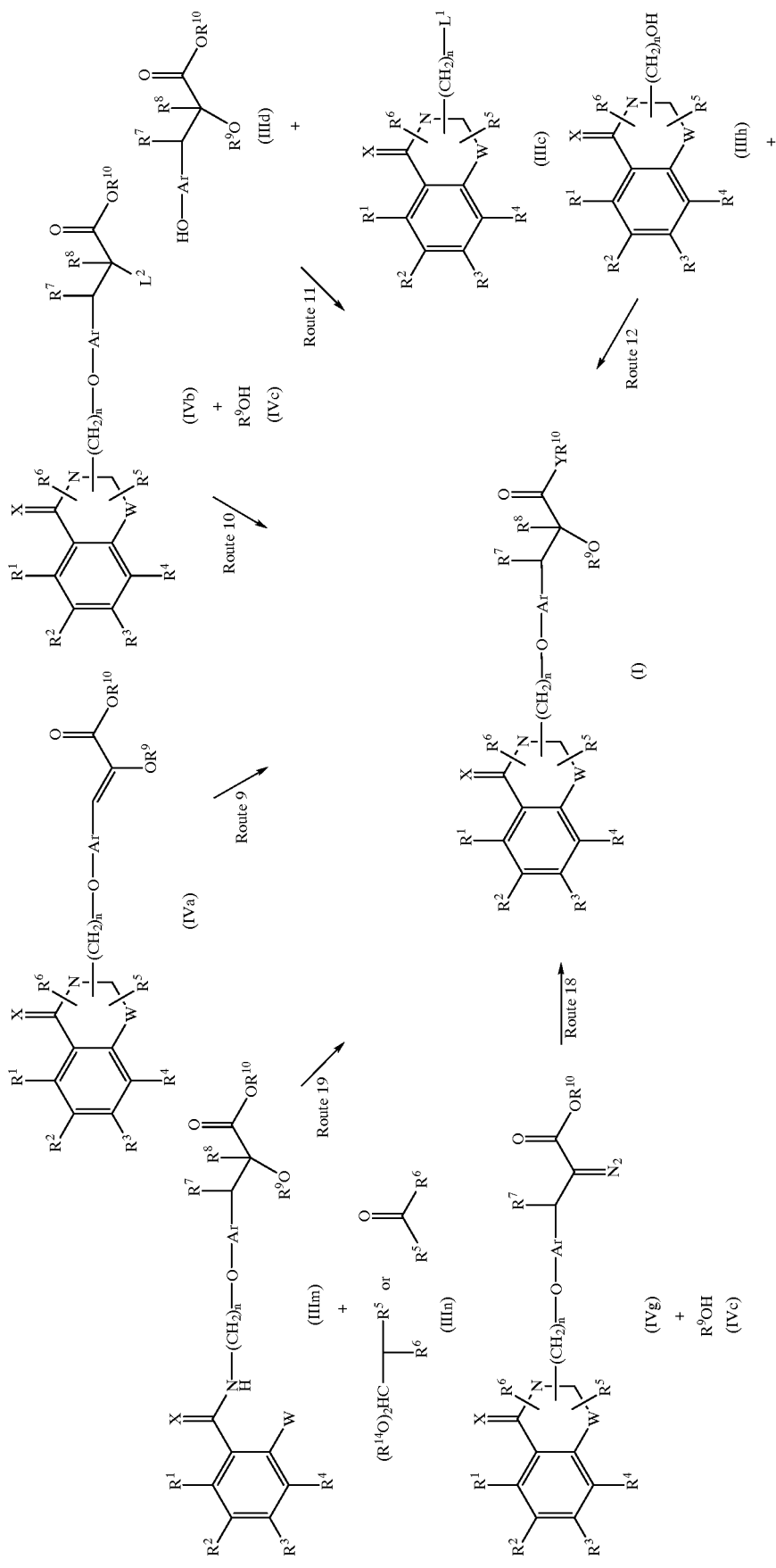

-continued
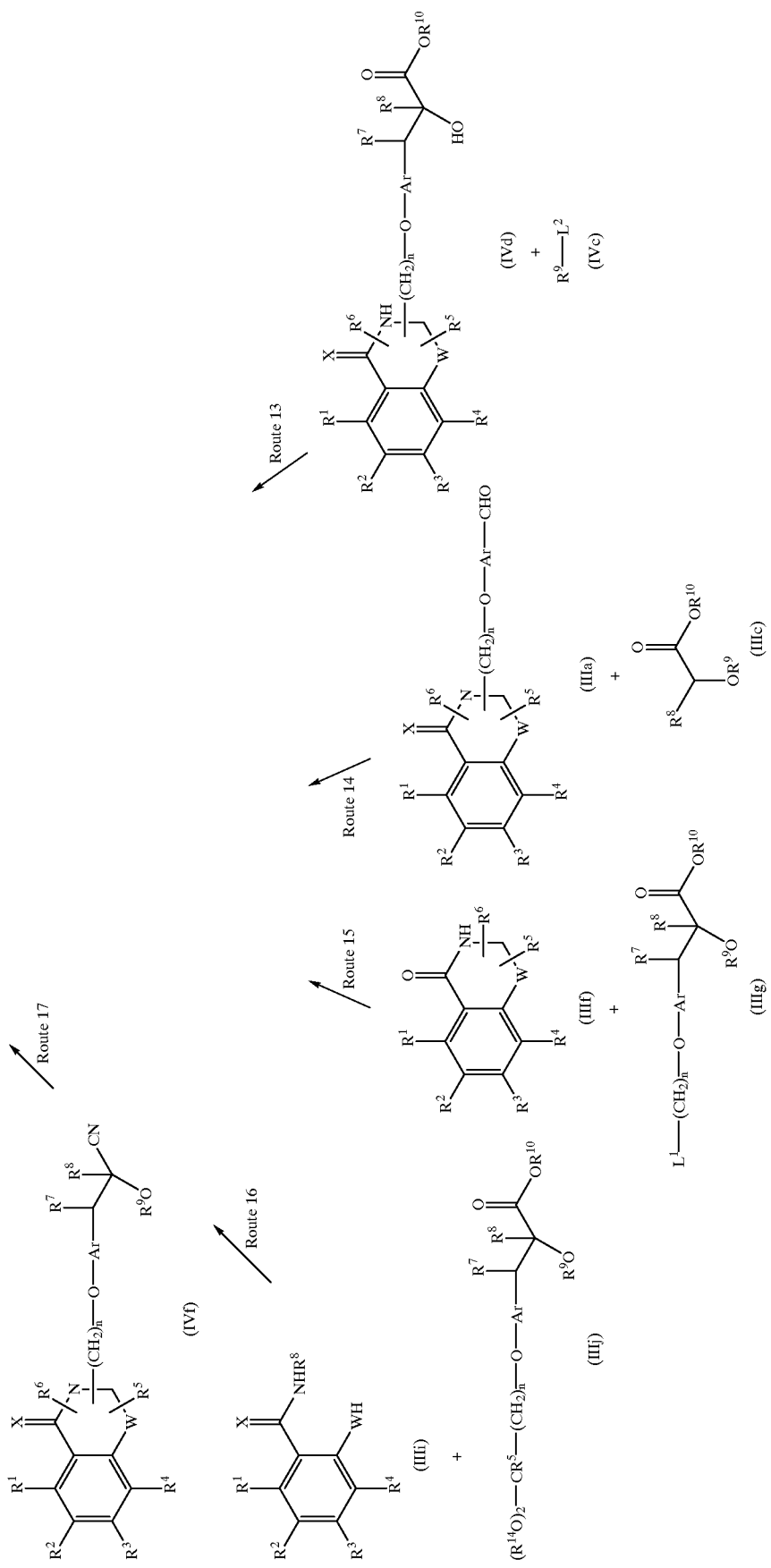

Route (9): The reduction of compound of the formula (IVa) which represents a compound of formula (I) where $R^7$ and $R^8$ together represent a bond, Y represent oxygen and all other symbols are as defined earlier, obtained as described earlier in Scheme-I, to yield a compound of the general formula (I) where $R^7$ and $R^8$ each represent hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. A pressure between atmospheric pressure and 80 psi may be employed The catalyst may be preferably 5–10% Pd/C and the amount of catalyst used may range from 50–300% w/w. The reaction may also be carried out by employing metal solvent reduction such as magnesium in alcohol or sodium amalgam in alcohol, preferably methanol. The hydrogenation may be carried out in the presence of metal catalysts containing chiral ligands to obtain a compound of formula (I) in optically active form. The metal catalyst may contain Rhodium, Ruthenium, Indium and the like. The chiaal ligands may preferably be chiral phosphines such as 2,3-bis(diphenylphosphino)butane, 1,2-bis(diphenyl-phosphino thane, 1,2-bis(2-methoxy phenylphosphino)ethane, 2,3-isopropylidene-2,3-dihydroxy-1,4-bis(diphenylphosphino)butane, 2,2'-bis(diphenylphosphino)-1,1'-binaphthyl and the like. Any suitable chiral catalyst may be employed which would give required optical purity of the product (I) (Ref: Principles of Asymmetric Synthesis, Tet. Org. Chem. Series Vol 14, pp 311–316, Ed. Baldwin J. E.).

Route (10): The reaction of compound of formula (IVb) where $R^{10}$ is as defined earlier excluding hydrogen atom and all other symbols are as defined earlier and $L^2$ is a leaving group such as halogen atom with a compound of general formula (IVc), where $R^9$ is as defined earlier excluding hydrogen atom to produce a compound of the formula (I) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as KOH, NaOH, NaOMe, NaOEt, $K^+BuO^-$ or NaH or mixtures thereof. Phase transfer catalysts such as tetraalkylammonium halides or hydroxides may be employed. The reaction temperature may range from 20° C.–120° C., preferably at a temperature in the range of 30° C.–100° C. The duration of the reaction may range from 1 to 12 hours, preferably from 2 to 6 hours. The compound of general formula (IVb) where the linker group —$(CH_2)_n$—O— is attached through carbon atom and its preparation has been disclosed in the copending U.S. application Ser. No. 08/982,911.

Route (11): The reaction of compound of formula (IIIe) defined earlier with a compound of formula (IIId) where all symbols are as defined earlier to produce a compound of the formula (I) may be carried out in the presence of solvents such as THF, DMF, DMSO, DME and the like or mixtures thereof The reaction,may be carried out in an inert atmosphere which is maintained by using inert gases such as $N_2$, Ar or He. The reaction may be effected in the presence of a base such as $K_2CO_3$, $Na_2CO_3$ or NaH or mixtures thereof Acetone may be used as a solvent when $K_2CO_3$ or $Na_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours. The compound of formula (IIId) may be prepared by Wittig Horner reaction between the protected hydroxyaryl aldehyde and compound of formula (IIIb) followed by reduction of the double bond and deprotection. Alternatively, the compound of formula (IIId) may be prepared by following a procedure disclosed in WO 94/01420.

Route (12): The reaction of compound of general formula (IIIh) defined earlier with a compound of general formula (IIId) where all symbols are as defined earlier to produce a compound of the formula (I) where all symbols are as defined above may be carried out using suitable coupling agents such as dicyclohexyl urea, triarylphosphine/dialkylaza-dicarboxylate such as $PPh_3$/DEAD and the like. The reaction may be carried out in the presence of solvents such as THF, DME, $CH_2Cl_2$, $CHCl_3$, toluene, acetonitrile, carbon tetrachloride and the like. The inert atmosphere may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route (13): The reaction of compound of formula (IVd) where all other symbols are as defined earlier with a compound of formula (IVe) where $R^9$ is as defined earlier excluding hydrogen atom and $L^2$ is a leaving group such as a halogen atom to produce a compound of formula (I) may be carried out in the presence of solvents such as THF, DMF, DMSO, DME and the like. The inert atmosphere may be maintained by using inert gases such as $N_2$, Ar or He. The reaction may be effected in the presence of a base such as KOH, NaOH, NaOMe, $K^+BuO^-$, NaH and the like. Phase transfer catalyst such as tetraalkylammonium halides or hydroxides may be employed. The reaction temperature may range from 20° C. to 150° C., preferably at a temperature in the range of 30 ° C. to 100° C. The duration of the reaction may range from 1 to 24 hours, preferably from 2 to 6 hours.

The compound of formula (IVd) represents compound of formula (I) where $R^9$ is hydrogen atom, Y is oxygen atom and all other symbols are as defined earlier.

The compound of general formula (IVd) may also be prepared from compound of formula (IVb), described in copending U.S. application Ser. No. 08/982,911 where $L^2$ is a halogen atom by reacting with formamide in the presence of water. Alternatively, it can be prepared from (IVa) by heating with aqueous alkali to 20° C. to 100° C. followed by reesterification of the hydrolysed acid.

Route (14): The reaction of a compound of the general formula (IIIa) as defined above with a compound of formula (IIIc) where $R^8$ is hydrogen and all other symbols are as defined earlier to produce a compound of formula (I) may be carried out under conventional conditions. The base is not critical. Any base normally employed for aldol condensation reaction may be employed, metal hydride such as NaH, or KH, metal alkoxides such as NaOMe, KOtbu, or NaOEt; metal amides such as $LiNH_2$, or $LiN(iPr)_2$. Aprotic solvent such as THF may be used. Inert atmosphere may be employed such as argon and the reaction is more effective under anhydrous conditions. Temperature in the range of −80° C. to $_{25}$° C. may be used. The β-hydroxyaldol product may be dehydroxylated using conventional methods, conveniently by ionic hydrogenation technique such as by treating with a trialkyl silane in the presence of an acid such as trifluoroacetic acid. Solvent such as $CH_2Cl_2$ may be used.

Favorably reaction proceeds at 25° C. Higher temperature may be employed if the reaction is slow.

Route (15): The reaction of a compound of general formula (IIIf) where all symbols are as defined earlier with a compound of general formula (IIIg) where all symbols are as defined earlier and $L^1$ is a leaving group such as halogen atom, p-toluenesulfonate, methanesulfonate, trifluoromethanesulfonate and the like, preferably a halogen atom, to produce a compound of general formula (I) defined above where the —$(CH_2)_n$—O—is attached through nitrogen atom may be carried out in the presence of solvents such as DMSO, DMF, DME, THF, dioxane, ether and the like or a combination thereof The reaction may be carried out in an inert atmosphere which may be maintained by using inert gases such as $N_2$, Ar, or He. The reaction may be effected in the presence of a base such as alkalis like sodium hydroxide or potassium hydroxide; alkali metal carbonates like sodium carbonate or potassium carbonate; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIf), preferably the amount of base ranges from 1 to 3 equivalents. The reaction may be carried out at a temperature in the range of 0° C. to 150° C., preferably at a temperature in the range of 15° C. to 100° C. The duration of the reaction may range from 0.25 to 24 hours, preferably from 0.25 to 6 hours.

Route (16): The reaction of compound of general formula (IIIi) where all symbols are as defined earlier, with a compound of formula (IIIj) where $R^{14}$ represents lower alkyl group and all other symbols are as defined earlier to produce a compound of formula (I) where the linker group —$(CH_2)_n$—O—is attached through carbon atom and all other symbols are as defined earlier, may be carried out in neat or in the presence of solvents such as THF, $CHCl_3$, benzene, toluene, hexane, dioxane and the like or mixture thereof. The reaction may be carried out at a temperature in the range of 0° C. to 250° C. preferably at a temperature in the range of 10° C. to 150° C. The reaction may be carried out in the presence of an acid or a base. The selection of acid or base is not critical. The examples of such acids include $H_2SO_4$, HCl, pTsOH, PPE (polyphosphoric ethyl ester) and the like. Examples of bases include pyrrolidine, piperidine and the like. The reaction may be carried out in an inert atmosphere which may be maintained by using inert gases such as $N_2$, Ar or He. The duration of the reaction may range from 0.25 to 24 h preferably, from 1 to 12 h.

The compound of general formula (IIIj), where all the symbols are as defined earlier may be prepared by a process which comprises, reacting a compound of the general formula (IVh)

$(R^{14}O)_2CR^5$—$(CH_2)_n$—$L^1$ (IVh)

where $R^{14}$ is a lower alkyl group and all other symbols are as defined earlier with a compound of general formula (IIId) where $R^7$, $R^8$, $R^9$, $R^{10}$ and Ar are as defined earlier.

The reaction of compound of formula (IVh) with compound of formula (IIId) to produce a compound of the formula (IIIj) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as $K_2CO_3$, $Na_2CO_3$ or NaH or mixtures thereof. The reaction temperature may range from 20° C.–120° C., preferably at a temperature in the range of 30° C.–80° C. The duration of the reaction may range from 1–12 hours, preferably from 2 to 6 hours.

Route (17): The conversion of compound of formula (IVf) where all symbols are defined above to a compound of formula (I) may be carried out either in the presence of a base or an acid and the selection of base or acid is not critical. Any base normally used for hydrolysis of nitrile to acid may be employed; metal hydroxides such as NaOH, or KOH in an aqueous solvent or any acid normally used for hydrolysis of nitrile to ester may be employed such as dry HCl in an excess of alcohol such as methanol, ethanol, propanol etc. The reaction may be carried out at a temperature in the range of 0° C. to reflux temperature of the solvent used, preferably at a temperature in the range of 25° C. to reflux temperature of the solvent used. The duration of the reaction may range from 0.25 to 48 hrs.

Route (18): The reaction of a compound of formula (IVg) where $R^{10}$ is as defined earlier excluding hydrogen atom and all other symbols are as defined earlier with a compound of formula (IVc) where $R^9$ is as defined earlier excluding hydrogen atom to produce a compound of formula (I) (by a rhodium carbenoid mediated insertion reaction) may be carried out in the presence of rhodium (II) salts such as rhodium (II) acetate. The reaction may be carried out in the presence of solvents such as benzene, toluene, dioxane, ether, THF and the like or a combination thereof or when practicable in the presence of $R^9OH$ as solvent at any temperature providing a convenient rate of formation of the required product, generally at an elevated temperature, such as reflux temperature of the solvent. The inert atmosphere may be maintained by using inert gases such as $N_2$, Ar or He. The duration of the reaction may range from 0.5 to 24 h, preferably from 0.5 to 6 h.

Route (19): The reaction of compound of general formula (IIIm), where $R^7$ and $R^8$ are as defined earlier, and all other symbols are as defined earlier with a compound of general formula (IIIn) where $R^{14}$ represents lower alkyl group and all other symbols are as defined earlier to produce a compound of general formula (I), where —$(CH_2)_n$—O—linker group is attached through nitrogen atom and all other symbols are as defined earlier may be carried out in neat or in the presence of solvents such as xylene, toluene, THF, dioxane, acetic acid, DMF, DMSO and the like or mixtures thereof. The reaction may be carried out in an inert atmosphere which may be maintained by using inert gases such as $N_2$, Ar or He. The reaction may be carried out at a temperature in the range of 50° C. to 200° C., preferably at a temperature in the range of 60° C. to 180° C. The reaction may be effected in the presence or in absence of a base or an acid. The nature of the base or the acid is not critical. Examples of such bases include organic bases such as pyridine, lutidine, triethyl amine, diisopropyl-ethyl amine and the like, metal carbonates such as $K_2CO_3$, $Na_2CO_3$. Examples of acids include organic acids such as AcOH, $C_2H_5COOH$, butyric acid, trifluoroacetic acid, p-toluenesulfonic acid, benzenesulfonic acid and the like, mineral acids such as HCl, HBr etc. The duration of the reaction may range from 0.25 to 48 hours, preferably from 0.50 to 18 hours.

The compound of general formula (I) where $R^{10}$ represents hydrogen atom may be prepared by hydrolysing a compound of formula (I) where $R^{10}$ represents all groups defined earlier except hydrogen using conventional methods. The hydrolysis may be carried out in the presence of a base such as $Na_2CO_3$ and a suitable solvent such as methanol, ethanol and the like or mixtures thereof The reaction may be carried out at a temperature in the range of 20–40° C., preferably at 25–30° C. The reaction time may range from 2 to 12 h, preferably from 4 to 8 h.

The compound of general formula (I) where Y represents oxygen and $R^{10}$ represents hydrogen or a lower alkyl group may be converted to compound of formula (I), where Y represents $NR^{10}$ by reaction with appropriate amines of the formula $NHR^{12}R^{12}$, where. $R^{10}$ and $R^{12}$ are as defined earlier. Suitably, the compound of formula (I) where $YR^{10}$ represents OH may be converted to acid halide, preferably $YR^{10}=Cl$, by reacting with appropriate reagents such as oxalyl chloride, thionyl chloride and the like, followed by treatment with amines of formula $NHR_{10}R_{12}$ where $R_{10}$ and $R_{12}$ are as defined earlier. Alternatively, mixed anhydrides may be prepared from compound of formula (I) where $YR^{10}$ represents OH and all other symbols are as defined earlier by treating with acid halides such acetyl chloride, acetyl bromide, pivaloyl chloride, dichlorobenzoyl chloride and the like. The reaction may be carried out in the presence of suitable base such as pyridine, triethylamine, diisopropyl ethyl amine and the like. Solvents such as halogenated hydrocarbons like $CHCl_3$, or $CH_2Cl_2$; hydrocarbons such as benzene, toluene, xylene and the like may be used. The reaction may be carried out at a temperature in the range of −40° C. to 40° C., preferably at a temperature in the range of 0° C. to 20° C. The acid halide or mixed anhydride thus prepared may further be treated with appropriate amines of formula $NHR^{10}R^{12}$ where $R^{10}$ and $R^{12}$ are as defined earlier.

In another embodiment of the present invention the novel intermediate of formula (IVf)

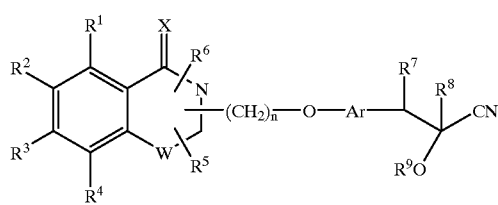

(IVf)

where X represents O or S; the groups $R^1$, $R^2$, $R^3$, $R^4$ and the groups $R^5$, and $R^6$ when attached to carbon atom may be same or different and represent hydrogen, halogen, hydroxy, cyano, nitro, formyl; or unsubstituted or substituted groups selected from alkyl, cycloalkyl, alkoxy, cycloalkyloxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, aminoalkyl, hydroxyalkyl, alkoxyalkyl, aryloxyalkyl, aralkoxy-alkyl, thioalkyl, alkylthio, alkoxycarbonylamino, aryloxycarbonylamino, aralkoxycarbonyl-amino, carboxylic acid or its derivatives, or sulfonic acid or its derivatives; W represents O, S or a group $NR^{11}$; $R^{11}$ and the groups $R^5$ and $R^6$ when attached to nitrogen atom may be the same or different and represent hydrogen, hydroxy, formyl or unsubstituted or substituted groups selected from alkyl, cycloalkyl, alkoxy, cycloalkoxy, aryl, aralkyl, aryloxy, aralkoxy, heterocyclyl, heteroaryl, heteroaryloxy, heteroaralkyl, heteroaralkoxy, acyl, acyloxy, hydroxyalkyl, amino, acylamino, alkylamino which may be mono or dialkylamino group, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, carboxylic acid derivatives, or sulfonic acid derivatives; n is an integer ranging from 1–4; Ar represents an unsubstituted or substituted divalent aromatic or heterocyclic group; $R^7$ represents hydrogen atom, hydroxy, alkoxy, halogen, lower alkyl, unsubstituted or substituted aralkyl group, or forms a bond with $R^8$; $R^8$ represents hydrogen atom, hydroxy, alkoxy, halogen, lower alkyl, acyl group, unsubstituted or substituted aralkyl, or $R^8$ forms a bond together with $R^7$; $R^9$ may be hydrogen or unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminocarbonyl, acyl, heterocyclyl, heteroaryl, or heteroaralkyl groups; the linking group represented by $—(CH_2)_n—O—$ may be attached either through nitrogen atom or carbon atom and a process for its preparation and its use in the preparation of β-aryl-α-substituted hydroxy alklaoic acids is provided (Scheme-III)

Scheme III

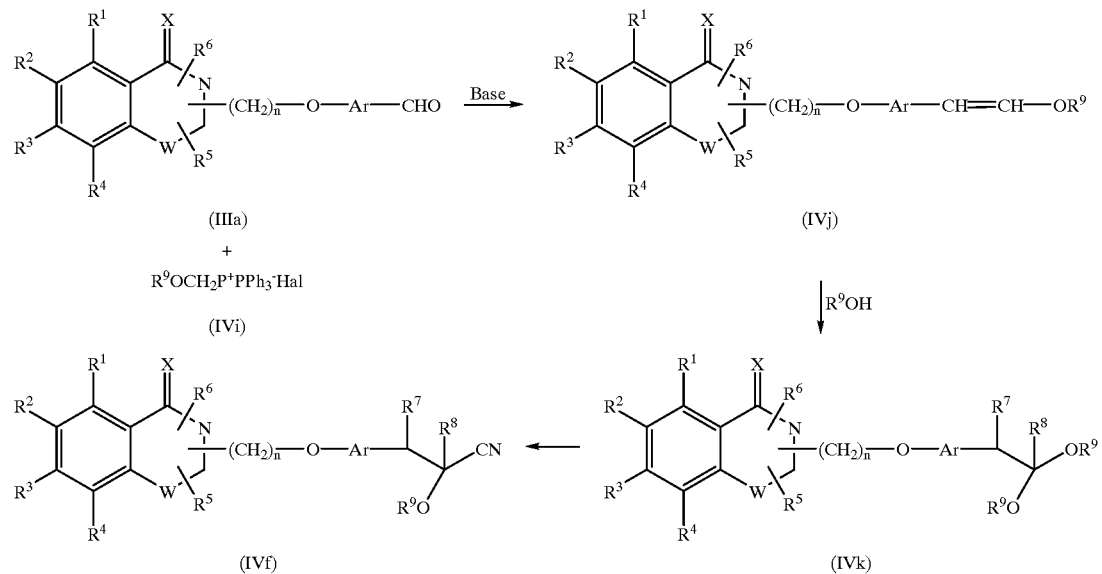

The reaction of a compound of formula (IIIa) where all symbols are as defined earlier with a compound of formula (IVi) where $R^9$ is as defined earlier excluding hydrogen and Hal represent a halogen atom such as Cl, Br, or I may be carried out under conventional conditions in the presence of a base. The base is not critical. Any base normally employed for Wittig reaction may be employed metal hydride such as NaH or KH; metal alkoxides such as NaOMe or $K^tBuO^-$ or NaOEt; or metal amides such as $LiNH_2$ or $LiN(iPr)_2$. Aprotic solvent such as THF, DMSO, dioxane, DME and the like may be used. Mixture of solvents may be used. HMPA may be used as cosolvent. Inert atmosphere may be employed such as argon and he reaction is more effective under anhydrous conditions. Temperature in the range of $-80°$ C. to $100°$ C. may be used. The compound of formula (IVj) where aHl symbols are as defined earlier may be onverted to a compound of formula (IVk) where $R^7$ and $R^8$ represent hydrogen atoms and all other symbols are as defined earlier, by treating with alcohol under anhydrous conditions in the presence of a strong anhydrous acid such as p-toluenesulfonic acid.

The compound of formula (IVk) defmed above upon. treatment with trialkylsilyl cyanide such as trimethylsilyl cyanide produces a compound of formula (IVf) where $R^7$ and $R^8$ represent hydrogen atoms and all other symbols are as defined earlier.

In still another embodiment of the present invention there is provided the novel intermediate of formula (IVg)

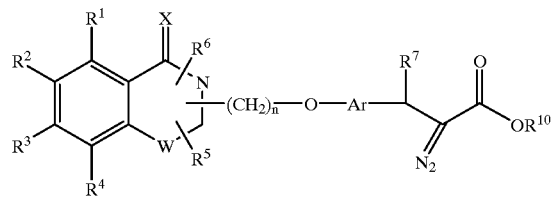
(IVg)

where X represents O or S; the groups $R^1$, $R^2$, $R^3$, $R^4$ and the groups $R^5$ and $R^6$ when attached to carbon atom may be the same or different and represent hydrogen, halogen, hydroxy, cyano, nitro, formyl; unsubstituted or substituted groups selected from alkyl, cycloalkyl, alkoxy, cycloalkyloxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, aminoalkyl, hydroxyalkyl, alkoxyalkyl, aryloxyalkyl, aralkoxyalkyl, thioalkyl, alkylthio, alkoxycarbonylamino, aryloxycarbonylamino, aralkoxycarbonyl-amino, carboxylic acid or its derivatives, or sulfonic acid or its derivatives; W represents O, S or a group $NR^{11}$; $R^{11}$ and the groups $R^5$ and $R^6$ when attached to nitrogen atom may be same or different and represent hydrogen, hydroxy, formyl or unsubstituted or substituted groups selected from all, cycloalkyl, alkoxy, cycloalkoxy, aryl, aralkyl, aryloxy, aralkoxy, heterocyclyl, heteroaryl, heteroaryloxy, heteroaralkyl, heteroaralkoxy, acyl, acyloxy, hydroxyalkyl, amino, acylamino, alkylamino which may be mono or dialkylamino group, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, carboxylic acid derivatives, or sulfonic acid derivatives; n is an integer ranging from 1–4; Ar represents an unsubstituted or substituted divalent aromatic or heterocyclic group; $R^7$ represents hydrogen atom, hydroxy, alkoxy, halogen, lower alkyl, or unsubstituted or substituted aralkyl group; $R^{10}$ may be hydrogen or unsubstituted or substituted groups selected from alkyl, cycloalkyl, aryl, aralkyl, heterocyclyl, heteroaryl, or heteroaralkyl groups; the linking group represented by $-(CH_2)_n-O-$ may be attached either through nitrogen atom or carbon atom and a process for its preparation and its use in the preparation of β-aryl-α-substituted hydroxyalkanoic acids is provided.

The compound of formula (IVg) where all other symbols are as defined earlier may be prepared by reacting a compound of formula (IVl)

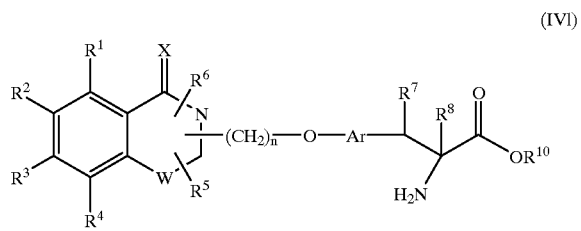
(IVl)

where $R^8$ is hydrogen atom and all other symbols are as defined earlier, with an appropriate diazotizing agent The diazotization reaction may be under conventional conditions. A suitable diazotizing agent is an alkyl nitrile, such as iso-amyl nitrile. The reaction may be carried out in presence of solvents such as THF, dioxane, ether, benzene and the like or a combination thereof Temperature in the range of $-50°$ C. to $80°$ C. may be used. The reaction may be carried out in an inert atmosphere which may be maintained by using inert gases such as $N_2$, Ar or He. The duration of the reaction may range from 1 to 24 h, preferably, 1 to 12 h.

The compound of formula (IVl) may also be prepared by a reaction between (IIIe) where all symbols are as defined earlier and a compound of formula (IVm)

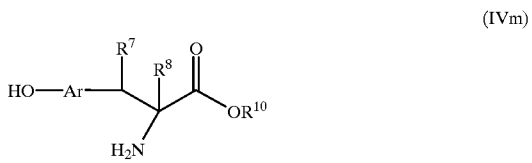
(IVm)

where $R^8$ is hydrogen atom and all other symbols are as defined earlier.

The reaction of compound of formula (IIIe) where all symbols are as defined earlier and a compound of formula (IVm) where all symbols are as defmed earlier may be carried out in the presence of solvents such as THF, DMF, DMSO, DME and the like or mixtures thereof The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof Acetone may be used as a solvent when $K_2CO_3$ or $Na_2CO_3$ is used as a base. The reaction temperature may range from $20°$ C.–$120°$ C., preferably at a temperature in the range of $30°$ C.–$80°$ C. The duration of the reaction may range from 1 to 24 hours, preferably from 2 to 12 hours.

In yet another embodiment of the present invention there is provided the novel termediates of formula (IIIm)

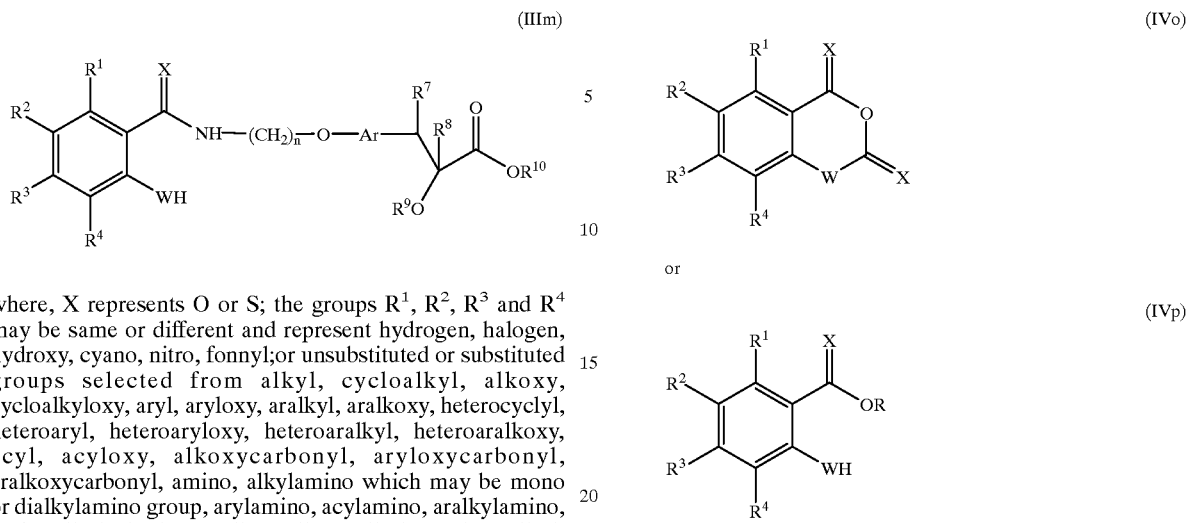

where, X represents O or S; the groups $R^1$, $R^2$, $R^3$ and $R^4$ may be same or different and represent hydrogen, halogen, hydroxy, cyano, nitro, fonnyl;or unsubstituted or substituted groups selected from alkyl, cycloalkyl, alkoxy, cycloalkyloxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, aminoalkyl, hydroxy-alky, alkoxyalkyl, aryloxyalkyl, aralkoxyalkyl, thioalkyl, alkylthio, alkoxycarbonylamino, aryloxycarbonylamino, aralkoxycarbonylamino, carboxylic acid or its derivatives, or sulfonic acid or its derivatives; W represents O, S or a group $NR^{11}$; $R^{11}$ represents hydrogen, hydroxy, fonnyl or unsubstituted or substituted groups selected from alkyl, cycloalkyl, alkoxy, cycloalkoxy, aryl, aralkyl, aryloxy, aralkoxy, heterocyclyl, heteroaryl, heteroaryloxy, heteroaralkyl, heteroaralkoxy, acyl, acyloxy, hydroxyalkyl, amino, acylamino, alkylamino which may be mono or dialkylamino group, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalklyl, carboxylic acid derivatives, or sulfonic acid derivatives; n is an integer ranging from 1–4; Ar represents an or unsubstituted or substituted divalent aromatic or heterocyclic group; $R^7$ represents hydrogen atom, hydroxy, alkoxy, halogen, lower alkyl, or unsubstituted or substituted aralkyl group or $R^7$ forms a bond with $R^8$; $R^8$ represents hydrogen atom, hydroxy, alkoxy, halogen, lower alkyl, acyl group, unsubstituted or substituted aralkyl, or $R^8$ forms a bond together with $R^7$; $R^9$ may be hydrogen or unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminoccrbonyl, acyl, heterocyclyl, heteroaryl, or heteroaralkyl groups; $R^{10}$ may be hydrogen or unsubstituted or substituted groups selected from alky, cycloalkyl, aryl, aralkyl, heterocyclyl, heteroaryl, or heteroaralkyl groups; the linking group represented by —$(CH_2)_n$—O—may be attached either through nitrogen atom or carbcn atom and a process for its preparation and its use in the preparation of β-aryl-α-oxysubstituted alkylcarboxylic acids is provided.

The compound of formula (IIIm) where all symbols are as defined above may be prepared by reacting a compound of formula (IVn)

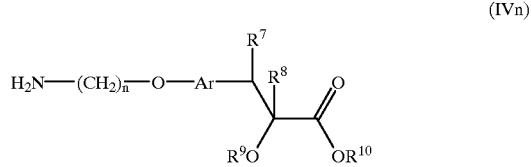

(IVn)

where all symbols are as defined earlier with a compound of formula (IVo) or (IVp)

The reaction of compound of formula (IVn) where all symbols are as defined earlier with a compound of formula (IVo) or (IVp) where $R^1$, $R^2$, $R^3$, $R^4$, W and X are as defined earlier to produce a compound of formula (IIIm) defined earlier may be carried out neat or in the presence of solvents such as xylene, toluene, dioxane, THF, DMF, DMSO, DME and the like or their mixtures. The reaction may be carried out in an inert atmosphere which is maintained by using inert gases such as $N_2$, Ar or He. The reaction temperature may range from 0° C.–150° C., preferably at a temperature in the range of 0° C.–120° C. The duration of the reaction may range from 0.5 to 12 hours, preferably from 0.5 to 6 hours.

The compound of formula (IVn) and its preparation has been disclosed in our copending application 09/179,002 filed Oct. 26, 1998.

The pharmaceutically acceptable salts are prepared by reacting the compound of formula (I) wherever applicable with 1 to 4 equivalents of a base such as sodium hydroxide, sodium methoxide, sodium hydride, potassium t-butoxide, potassium hydroxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^{10}$ represents OH may be converted to a 1:1 mixture of diastereomeric amides by treating with optically active amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The compounds of general formula (I) are useful in the treatment and/or prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis and for the treatment of cancer. The compounds of the present inventions are useful in the treatment and/or prophylaxis of arteriosclerosis and/or xanthoma in combination with one or more HMG CoA reductase inhibitors, hypolipidemic/hypolipoproteinemic agents such as fibric acid derivatives, nicotinic acid, cholestyramnine, colestipol, or probucol. The compounds of the present invention in combination with HMG CoA reductase inhibitors, and/or hypolipidernic/hypolipoproteinemic agents can be administered together or within such a period to act synergistically. The HMG CoA reductase inhibitors may be selected from those used for the treatment or prevention of hyperlipidemia such as lovastatin, provastatin, simvastatiu, fluvastatin, atorvastatin, cerivastatin and their analogs thereof. Suitable fibric acid derivative may be gemfibrozil, clofibrate, fenofibrate, ciprofibrate, benzafibrate and their analogs thereof.

The present invention also provides a pharmaceutical composition, containing the compounds of the general formula (I), as defined above, their tautomeric forms, their derivatives, their analogs, their stereoisomers, their polymorphs, their pharmaceutically acceptable salts, their pharmaceutically acceptable solvates in combination with the usual pharmaceutically employed carriers, diluents and the like.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral admnistration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The present invention is explained in detail in the examples given which are provided by way of illustration only and therefore should not to be construed to limit the scope of the invention.

PREPARATION 1

Ethyl 2-ethoxy-3-[4-[(2,2-diethoxy)ethoxy]phenyl]-2-propenoate

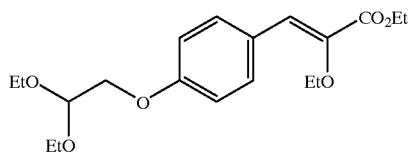

To a stirred suspension of sodium hydride (756 mg, 32 mmol, 95%) in dry THF (60 mL) was added a solution of ethyl(diethylphosphono)ethoxyacetate (6.20 g, 23.1 mmol) in THF (20 mL) at 0–5° C. dropwise and stirred for 30 min at 5–25° C. To the reaction mixture was added a solution of 4-[(2,2-diethoxy)ethoxy]benzaldehyde (5.0 g, 21.0 mmol) in THF (10 mL) at 25° C. and stirred further for 30 min. After completion of the reaction (TLC monitored), THF was removed and the resultant residue was diluted with water (100 mL) and extracted with ethyl acetate (3×25 mL). The combined organic extracts were washed with brine, dried over anhydrous Na$_2$SO$_4$ and concentrated to yield the title compound (6.5 g, 88%) as a mixture of E/Z isomers.

$^1$H NMR (CDCl$_3$): δ 7.75 (d, J=8.77 Hz, 2H), 6.96 (s, 1H), 6.92 (d, J=8.77 Hz, 2H), 4.84 (t, J=5.12 Hz, 1H), 4.29 (q, J=7.10 Hz, 2H), 4.10–3.90 (m, 4H), 3;90–3.55(m, 4H), 1.37 (t, J=7.10 Hz, 6H), 1.25 (t, J=7.03 Hz, 6H).

PREPARATION 2

Methyl 2-ethoxy-3-[4-[(2,2-diethoxy)ethoxy]phenyl]propanoate

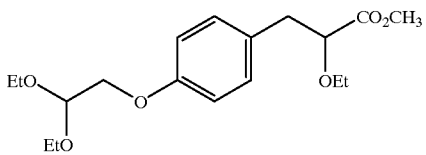

A mixture of ethyl 2-ethoxy 3-[4-[(2,2-diethoxy)ethoxy] phenyl]-2-propenoate (500 mg, 1.42 mmol) obtained in preparation 1, and magnesium turnings (340 mg, 14.2 mmol) in methanol (15 mL) was stirred at 45–50° C. until the reaction started (as evidenced by hydrogen evolution). On initiation of the reaction, the mixture was stirred at 25° C. for a further 2 h. The reaction mixture was added to ice water (15 mL), the pH adjusted to 7.5–8.0 using 10% aqueous hydrochloric acid, and the solution extracted with ethyl acetate (3×50 mL). The combined organic extracts were washed with brine, dried over anhydrous Na$_2$SO$_4$ and concentrated. The residue was chromatographed on silica gel using a gradient of 5–15% ethyl acetate in pet ether as eluent to afford the title compound (436 mg, 87%).

$^1$H NMR (CDCl$_3$): δ 7.14 (d, J=8.50 Hz, 2H), 6.84 (d, J=8.50 Hz, 2H), 4.82 (t, J=5.15 Hz, 1), 4.05–3.92 (m, 1H), 3.97 (d, J=5.15 Hz, 2H), 3.85–3.50 (m, 5H), 3;70 (s, 3H), 3.45–3.25 (m, 1H), 2.95 (d, J=6.64 Hz, 2H), 1.25 (t, J=7.03 Hz, 6H), 1;16 (t, J=7.0 Hz, 3H).

PREPARATION 3

Ethyl 2-phenoxy-3-[4-[(2,2-diethoxy)ethoy]phenyl]-2-propenoate

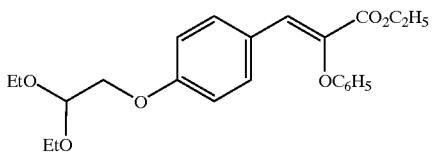

The title compound (2.25 g, 65%) as a mixture of E/Z isomers was obtained from 4-[(2,2-diethoxy)ethoxy] benzaldehyde (2.05 g, 8.63 mmol), ethyl(diethylphosphono) phenoxy-acetate (3.0 g, 9.49 mmol) and NaH (310 mg, 12.94 mmol, 95%) by a similar procedure to that described in preparation 1.

$^1$H NMR (CDCl$_3$): δ 7.50–7.20 (m, 5H), 7.15–6.95 (m, 2H), 6.95–6.70 (m, 3H), 4.90–4.70 (m, 1H), 4.30–4.08 (m, 2H), 4.03 (t, J=6.80 Hz, 2H), 3.90–3;50 (m, 4H), 1.30–1.10 (m, 9H).

PREPARATION 4

Methyl 2-phenoxy-3-[4-(2,2-diethoxy)ethoxy]phenyl]propanoate

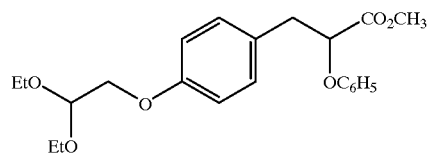

The title compound (1.36 g, 66%) was obtained as a liquid from ethyl 2-phenoxy-3-[4-[(2,2-diethoxy)ethoxy]phenyl]-2-propenoate (2.05 g, 5.1 mmol) obtained in preparation 3 and magnesium turnings (1.23 g, 51 mmol) by a similar procedure to that described in preparation 2.

$^1$H NMR (CDCl$_3$): δ 7.35–7.15 (m, 5H), 7.0–6.8 (m, 4H), 4.76 (t, J=5.20 Hz, 1H), 3.98 (d, J=5.2 Hz, 2H), 3.8–3.5 (m, 5H), 3.71 (s, 3H), 3.18 (d, J=6.96 Hz, 2H), 1.24 (t, J=7.01 Hz, 6H).

EXAMPLE-1

Ethyl 2-ethoxy-3-[4-[2-[4-oxo-3,4-dihydro-1,3-benzoxazin-3-yl]ethoxy]phenyl]-2-propenoate

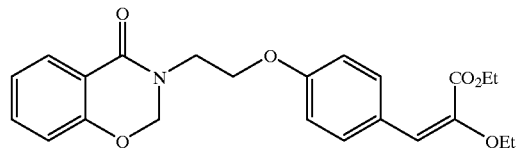

The title compound (4.7 g, 76%) was obtained as a white solid from 4-[2-[4-oxo-3,4-dihydro-1,3-benzoxazin-3-yl] ethoxy]benzaldehyde (4.5 g, 15.15 mmol), ethyl(diethyl-phosphono)ethoxy acetate (4.9 g, 18.18 mmol) and NaH (545 mg, 22.73 mmol) by a similar procedure to that described in preparation 1: mp 81–83° C.

$^1$H NMR (CDCl$_3$): δ 7.95 (d, J=6.64 Hz, 1H), 7.74 (d, J=8.72 Hz, 2H), 7.44 (t, J=6.86 Hz, 1H), 7.20–7.00 (m, 2H), 7.02–6.80 (m, 3H), 5.37 (s, 2H), 4.40–4.05 (m, 4H), 4.05–3.80 (m, 4H),1.50–1.20 (m, 6H).

EXAMPLE-2

(±)-Ethyl 2-ethoxy-3-[4-[2-[4-oxo-3,4-dihydro-1,3-benzoxazin-3-yl]ethoxy]phenyl]propanoate

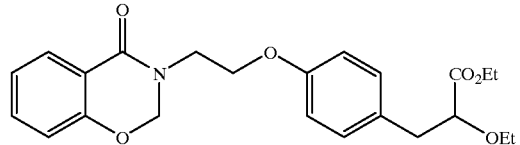

A solution of ethyl 2-ethoxy-3-[4-[2-[4-oxo-3,4-dihydro-1,3-benzoxazin-3-yl]-ethoxy]phenyl]-2-propenoate (4.5 g, 10.5 mmol) obtained in Example 1, in 1,4-dioxane (50 mnl) was reduced with hydrogen in the presence of 10% palladium charcoal (450 mg) at 50–60 psi for 12 h. The reaction mixture was filtered through a bed of celite and the celite bed was washed with 1,4-dioxane. The filtrate was evaporated to dryness under reduced pressure to yield the title compound (3.5 g, 78%): mp 78–80° C.

¹H NMR (CDCl₃): δ 7.90 (d, J=7.56 Hz, 1H), 7.44 (t, J=7.05 Hz, 1H), 7.26–7.07 (m, 3H), 6.97 (d, J=8.30 Hz, 1H), 6.80 (d, J=8.62 Hz, 2H), 5.37 (s, 2H), 4.21–4.11 (m, 4H), 3.98–3.92 (m, 3H), 3.63–3.55 (m, 1H), 3.37–3.29 (m, 1H), 2.93 (d, J=1.23 Hz, (t, J=7.10 Hz, 3H), 1.16 (t, J=7.05 Hz, 3H).

EXAMPLE-3

(±)-2-Ethoxy-3-[4-[2-[4-oxo-3,4-dihydro-1,3-benzoxazin-3-yl]ethoxy]phenyl]propanoic acid

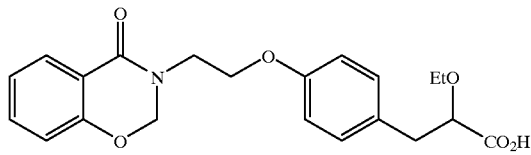

To a stirred solution of ethyl 2ethoxy-3-[4-[2-[4-oxo-3,4-dihydro-1,3-benzoxazin-3-yl]ethoxy]phenyl]propanoate (3.5 g, 8.5 mmol), obtained in Example 2, in methanol (25 mL) was added a solution of sodium carbonate (4.5 g, 42.5 mmol) in water (25 mL) and stirred for 5 h at 25–30° C. Methanol was removed under reduced pressure and the aqueous layer was washed with ethylacetate. The aqueous layer was acidified to pH 2.0 with 2N HCl. The white solid precipitated was filtered and dried to yield the title compound (3.04 g, 93%): mp 103–105° C.

¹H NMR (CDCl₃): δ 8.05 (d, J=6.70 Hz, 1H), 7.54 (t, J=7.30 Hz, 1H), 7.25 (d, J=8.20 Hz, 2H), 7.20 (t, J=7.30 Hz, 1H), 7.06 (d, J=8.20 Hz, 1H), 6.90 (d, J=8.41 Hz, 2H), 5.46 (s, 2 H), 4.27 (t, J=4.70 Hz, 2H), 4.11–3.90 (m, 1H), 4.05 (t, J=4.70 Hz, 2H), 3,80–3.60 (m, 1H), 3.60–3.40 (m, 1H), 3.14 (dd, J=14.10 and 4.27 Hz, 1H), 3.04 (dd, J=14.20 and 7.50 Hz, 1H), 1.26 (t, J=7.07 Hz, 3H).

EXAMPLE-4

(±)-Sodium 2-ethoxy-3-[4-[4-oxo-3,4-dihydro-1,3-benzoxazin-3-yl]ethoxy]phenyl]propanoate

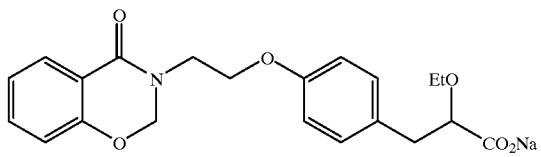

To a stirred suspension of (±)-2-ethoxy-3-[4-[2-[4-oxo-3,4-dihydro-1,3-benzoxazin-3-yl]ethoxy]phenyl]propanoic acid (100 mg, 0.26 mmol), obtained in Example 3 in methanol (3 mL) was added a solution of sodium methoxide (54 mg, 1.0 mmol) in methanol (1 mL) dropwise at 30° C. The reaction mixture was stirred for further 1 h. Diethylether (5 mL) was added and the white solid precipitated was filtered and dried to afford the title compound (85 mg, 80%): mp 186–188° C.

¹H NMR (CDCl₃): δ 7.83 (d, J=7.56 Hz, 1H), 7.56 (t, J=7.68 Hz, 1H), 7.21–7.07 (m, 4H), 6.84 (d, J=8.39 Hz, 2H), 5.43 (s, 2 H), 4.13 (t, J=5.19 Hz, 2H), 3.87 (t, J=5.02 Hz, 2H), 3.62–3.48 (m, 2H), 3.12 (t, J=4.36 Hz, 1H), 2.86 (dd, J=14.12 and 3.32 Hz, 1H), 2.61 (dd, J=14.12 and 9.04 Hz, 1H), 0.98 (t, J=7.01 Hz, 3H).

EXAMPLE-5

(+)-Ethyl 2-ethoxy-3-[4-[2-[4-oxo-3,4-dihydro-1,3-benzoxazin-3-yl]ethoxy]phenyl]propanoate

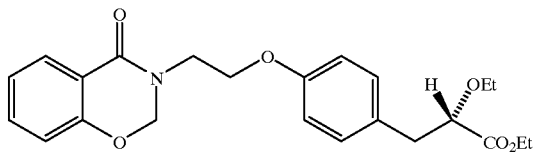

To a stirred mixture of 3-(2-hydroxyethyl)-4-oxo-3,4-dihydro-1,3-benzoxazine (325 mg, 1.68 mmol) and triphenylphosphine (660 mg, 2.52 mmol) in toluene (10 mL) was added a solution of (+)-ethyl 2-ethoxy-3-(4-hydroxyphenyl) propanoate (400 mg, 1.68 mmol) at 25° C. and stirred for 10 min. To the reaction mixture was added diisopropyldiazodicarboxylate (0.5 mL, 2.52 mmol) at 25–30° C. and stirred for further 40 h. Water was added to the reaction mixture and extracted with ethyl acetate (3×10 mL). The combined organic extracts were washed with brine, dried over anhydrous Na₂SO₄ and concentrated. The residue was chromatographed on silica gel using a gradient of 5–15% ethyl acetate in pet ether as eluent to afford the title compound (527 mg, 76%): mp 76–78° C.

$[\alpha]_D^{25}$ 12.2 (C=0.5, MeOH);

¹H NMR (CDCl₃): δ 7.94 (d, J=7.8 Hz, 1H), 7.44 (t, J=7.72 Hz, 1H), 7.17–6.95 (m, 6H), 6.79 (d, J=8.30 Hz, 2H), 5.38 (s, 2H), 4.22–4.11 (m, 3H), 3.95 (t, J=2H), 3.63–3.55 (m, 1H), 3.37–3.29 (m, 1H), 2.93 (d, J=6.64 Hz, 2H), 1.22 (t, J=7.06 Hz, 3H), 1.15 (t, J=7.05 Hz, 3H).

EXAMPLE-6

(–)-Ethyl 2-ethoxy-3-[4-[2-[4-oxo-3,4-dihydro-1,3-benzoxazin-3-yl]ethoxy]phenyl]propanoate

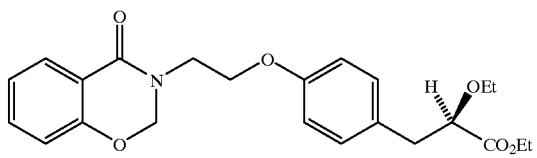

The title compound (500 mg, 64%) was obtained from 3-(2-hydroxyethyl)-4-oxo-3,4-dihydro-1,3-benzoxazine (364 mg, 1.89 mmol), (–)-ethyl 2ethoxy-3-(4-hydroxyphenyl) propanoate (450 mg, 1.89 mmol), triphenylphosphine (745 mg, 2.84 mmol) and diisopropyl-diazodicarboxylate (575 mg, 2.84 mmol) by a similar procedure to that described in Example 5: mp 76–78° C.

$[\alpha]_D^{25}$ =–11.96 (C=0.51, MeOH);

¹H NMR (CDCl₃): δ 7.95 (d, J=7.75 Hz, 1H), 7.43 (t, J=7.45 Hz, 1H), 7.22–7.03 (m, 3H), 6.97 (d, J=7.75 Hz, 1H), 6.79 (d, J=8.63 Hz, 2 H), 5.37 (s, 2H), 4.22–4.05 (m, 4H), 4.05–3.86 (m, 3H), 3.70–3.50 (m, 1H), 3.41–3.20 (m, 1H), 2.93 (d, 1.22 (t, J=7.05 Hz, 3H), 1.15 (t, J=7.05 Hz, 3H).

EXAMPLE-7

[2R, N(1S)]2-Ethoxy-3-[4-[2-[4-oxo-3,4-dihydro-1,3-benzoxazin-3-yl]ethoxy]phenyl]-N-(2-hydroxy-1-phenylethyl)propanamide (7a)

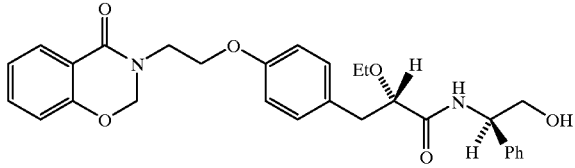

[2S, N(1S)]2-Ethoxy-3-[4-[2-[4-oxo-3,4-dihydro-1,3-benzoxazin-3-yl]ethoxyl]phenyl]-N-(2-hydroy-1-phenylethyl)propanamide (7b)

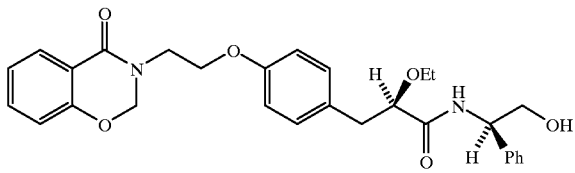

To a stirred solution of 2-ethoxy-3-[4-[2-[4-oxo-3,4-dihydro-1,3-benzoxazin-3-yl]ethoxy]phenyl]propanoic acid (500 mg, 1.30 mmol) obtained in Example 3, in dry dichloromethane (6 mL) was added triethylamine (0.45 μL, 3.24 mmol) at 0° C., followed by addition of pivaloyl chloride (180 mg, 1.5 mmol) and stirred for 30 min. at the same temperature. To this reaction mixture was added a solution of (S)(+)-2-phenylglycinol (180 mg, 1.3 mmol) in dichloromethane (2 mL) containing triethylamine (0.37 mL, 2.6 mmol). After stirring for 1 h, dichloromethane (10 mL) was added and the mixture was washed with water, brine, dried over anhydrous $Na_2SO_4$ and evaporated. The residue was chromatographed on silica gel using a gradient of 10–50% ethyl acetate in pet ether as eluent to afford firstly a diastereomer tentatively assigned as [2R,N(1S)]2-ethoxy-3-[4-[2-[4-oxo-3,4,-dihydro-1,3-benzoxazin-3-yl]ethoxy]phenyl]-N-(2-hydroxy-1-phenylethyl)propanamide (7a) followed by [2S, N(1 S)]2-ethoxy-3-[4-[2-[4-oxo-3,4-dihydro-1,3-benzoxazin-3-yl]ethoxy]phenyl]-N-(2-hydroxy-1-phenylethyl) propanamide (7b).

Spectral Data for 7a:

$[\alpha]_D^{25}$=43.8 (C=0.5, MeOH). mp: 64–68° C.;

$^1$H NMR (CDCl$_3$): δ 7.94 (d, J=7.80 Hz, 1H), 7.44 (t, J=7.38 Hz, 1H), 7.40–7.26 (m, 3H), 7.26–7.10 (m, 4H), 7.10–6.95 (m, 2H), 6.82 (d, J=8.40 Hz, 5.37 (s, 2H), 5.07–4.90 (m, 1H), 4.20 (t, J=4.63 Hz, 2H), 4.06–3.90 (m, 3H), 3.69–3.65 (m, 2H), 3.48 (q, J=7.00 Hz, 2H), 3.11 (dd, J=14.10 and 3.74 Hz, 1H), 2.92 (dd, J=14.10 and 6.23 Hz, 1H), 1.14 (t, J=7.00 Hz, 3H).

Spectral data for 7b:

$[\alpha]_D^{25}$=5.20 (C=0.5, MeOH). mp: 88–92° C.;

$^1$H NMR (CDCl$_3$): δ 7.97 (d, J=7.75 Hz, 1H), 7.46 (t, J=7.75 Hz, 1H), 7.26 (d, J=8.40 Hz, 1H), 7.30–6.95 (m, 7H), 6.73 (d, J=8.40 Hz, 2H), 5.40 (s, 2H), 5.08–4.95 (m, 1H), 1H), 4.16 (t, J=4.70 Hz, 2H), 4.05–3.92 (m, 3H), 3.90–3.82 (m, 2H), 3.54 (q, J=6,75 Hz, 2H), 3.10 (dd, J=14.10 and 3.74 Hz, 1H), 2.90 (dd, J=14.10 and 6.73 Hz, 1H), 1,19 (t, J=7.01 Hz, 3H).

EXAMPLE-8

(+)-2-Ethoxy-3-[4-[2-[4-oxo-3,4-dihydro-1,3-benzoxazin-3-yl]ethoxy]phenyl]propanoic acid

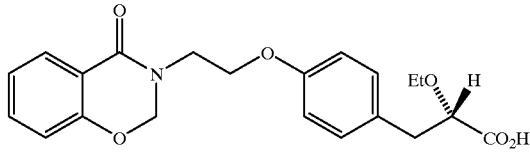

Method A

A solution of [2R, N(1S)] 2-ethoxy-3-[4-[2-[4-oxo-3,4-dihydro-1,3benzoxazin-3-yl]ethoxy]phenyl]-N-(2-hydroxy-1-phenylethyl)propanamide (1.60 g, 3.17 mmol) obtained in Example 7a, in a mixture of 1M sulphuric acid (40 mL) and dioxanewater (1:1, 144 mL) was heated at 100° C. for 16 h. The reaction mixture was cooled to 25° C. and dioxane was removed under reduced pressure. The remaining aqueous layer was extracted wit ethyl acetate (3×50 mL). The combined organic extracts were washed with brine, dried over anhydrous $Na_2SO_4$ and concentrated to yield the title compound (950 mg, 78%).

Method B

The title compound (116 mg, 83%) was obtained from (+)-ethyl 2-ethoxy-3-[4-[2-[4-oxo-3,4-dihydro-1,3-benzoxazin-3-yl]ethoxy]phenyl]propanoate (150 mg, 0.36 mmol) obtained in Example 5, and sodium carbonate (192 mg, 1.8 mmol) by a similar procedure to that described in Example 3: mp 88–90° C.

$[\alpha]_D^{25}$=18.0 (C=0.5, MeOH);

$^1$H NMR (CDCl$_3$): δ 7.90 (d, J=7.66 Hz, 1H), 7.46 (t, J=7.60 Hz, 1H), 7.17 (d, J=8.40 Hz, 2H), 7.12 (t, J=7.60 Hz, 1H), 6.98 (d, J=7.60 Hz, 1H), 6.82 (d, J=8,40 Hz, 2H), 5.38 (s, 2H), 4.19 (t, J=4.70 Hz, 2H), 4.04 (dd, J=7.35 and 4.35 Hz, 1H), 3.97 (t, J=4.70 Hz, 2H), 3.72–3.53 (m, 1H), 3.53–3.38 (m, 1H), 3.12 (dd, J=14.11 and 4.35 Hz, 1H), 2.95 (dd, J=14.11 and 7.35 Hz, 1H), 1.17 (t, J=7.05 Hz, 3H).

EXAMPLE-9

(−)-2-Ethoxy-3-[4-[2-[4oxo-3,4-dihydro-1,3-benzoxazin-3-yl]ethoxy]phenyl]propanoic acid

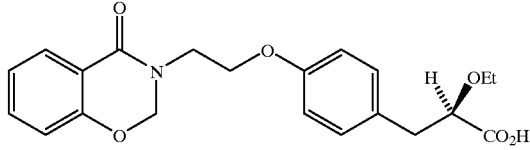

Method A

The title compound (780 mg, 81%) was obtained from [2S, N(1S)] 2-ethoxy-3-[4-[2-[4-oxo-3,4-dihydro-1,3-benzoxazin-3-yl]ethoxy]phenyl]-N-(2-hydroxy-1-phenylethyl) propanamide (1.03 g, 2.5 mmol) obtained in Example 7b, by a similar procedure described in Example 8 Method A.

Method B

The title compound (130 mg, 94%) was obtained from (−)-ethyl 2-ethoxy-3-[4-[2-[4-oxo-3,4-dihydro-1,3- benzoxazin-3-yl]ethoxy]phenyl]propanoate (149 mg, 0.36 mmol) obtained in Example 6, and sodium carbonate (384 mg, 1.8 mmol) by a similar procedure to that described in Example 3: mp 91–93° C.

$[\alpha]_D^{25}$=−19.8 (C=0.5, MeOH);

$^1$H NMR (CDCl$_3$): δ 7.96 (d, J=7.80Hz, 1H), 7.46 (t, J=7.80 Hz, 1H), 7.16 (d, J=8.45 Hz, 2H), 7.12 (t, J=7.40 Hz, 1H), 6.98 (d, J=7.40 Hz, 1H), 6.82 (d, J=8.45 Hz, 2H),5.38 (s, 2H), 4.19 (t, J=4.75 Hz, 2H), 4.05 (dd, J=7.35 and 4.40 Hz, 1H), 3.96 (t, J=4.75 Hz, 2H), 3.70–3.50 (m, 1H), 3.50–3.33 (m, 1H), 3.09 (dd, J=14.11 and 4.40 Hz, 1H), 2.95 (dd, J=14.11 and 7.35 Hz, 1H), 1.18 (t, J=7.01 Hz, 3H).

EXAMPLE-10

(±)-Ethyl 2-phenoxy-3-[4-[2-[4-oxo-3,4-dihydro-1, 3-benzoxazin-3-yl]ethoxy]phenyl]-2-propenoate

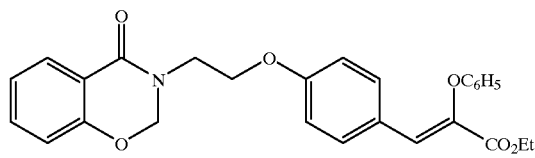

The title compound (520 mg, 56%) as a mixture of E/Z isomer was obtained from 4-[2-[4-oxo-3,4-dihydro-1,3-benzoxazin-3-yl]ethoxy]benzaldehyde (594 mg, 2.0 mmol), ethyl(diethyl phosphono)phenoxyacetate (695 mg, 2.2 mmol) (J. Org. Chem., 1983, 48, 3407) and sodium hydride (75 mg, 3.0 mmol, 95%) as a base by a similar procedure to that described in preparation 1: mp 104–106° C.

$^1$H NMR (CDCl$_3$): δ 8.05–7.90 (m, 1H), 7.67 (d, J=8.60 Hz, 1H), 7.60–7.20 (m, 5H), 7.20–6.95 (m, 4H), 6.95–6.80 (m, 2H), 6.72 (s, 1H), 5.39 and 5.35 (s, 2H), 4.40–4.08 (m, 4H), 4.08–3.90 (m, 2H), 1.20 and 1.07 (t, J=7.05 Hz, 3H).

EXAMPLE-11

(±)-Ethyl 2-ethoxy-3-[4-[2-[2, 2-dimethyl-4-oxo-3, 4-dihydro-1,3-benzoxazin-3-yl]ethoxy]phenyl] propanoate

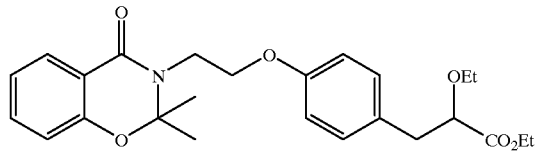

To a stirred solution of 2,2-dimethyl-4-oxo-3,4-dihydro-1,3-benzoxazine (0.3 g, 1.69 mmol) in DMF (3 mL) was added potassium carbonate (0.47 g, 3.39 mmol) and stirred for 30 min. To this reaction mixture was added a solution of ethyl 2-ethoxy-3-[4-(2-bromoethoxy) phenyl]propanoate (0.70 g, 2.03 mmol) (disclosed in U.S. patent application Ser. No. 09/012, 585) in DMF (1mL) and stirred for 24 h at 60–70° C. The reaction mixture was diluted with water and extracted with ethyl acetate (3×10 mL). The combined organic extracts were washed with brine, dried over anhydrous Na$_2$SO$_4$ and concentrated. The residue was chromatographed on silica gel using a gradient of 5–15% of ethyl acetate in pet ether as eluent to afford the title compound (0.34 g, 45%) as a liquid.

$^1$HNMR (CDCl$_3$): δ 7.91 (d, J=7.50 Hz, 1H), 7.43 (t, J=7.50 Hz, 1H), 7.15 (d, J=8.35 Hz, 2H), 7.06 (t, J=7.50 Hz, 1H), 6.89 (d, J=7.50 Hz, 1H), 6.82 (d, J=8.35 Hz, 2), 4.28–4.05 (m, 4H), 4.05–3.80 (m, 3H), 3.70–3.50 (m, 1H), 3.50–3.22 (m, 1H), 2.93 (d, J=6.65 Hz, 2H), 1.74 (s, 6H), 1.22 (t, J=7.05 Hz, 3H); 1.15 (t, J=6.95 Hz, 3H).

EXAMPLE-12

(±)-2-Ethoxy-3-[4-[2-[2,2-dimethyl-4-oxo-3,4-dihydro-1,3-benzoxazin-3-yl] ethoxy]phenyl] propanoic acid

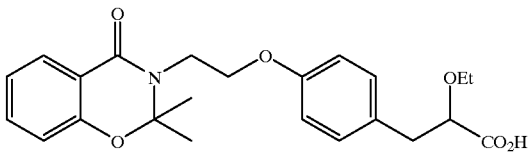

The title compound (105 mg, 75%) was obtained from (±)-ethyl 2-ethoxy-3-[4-[2-[2,2-dimethyl-4-oxo-3,4-dihydro-1,3-benzoxazin-3-yl]ethoxy]pheny]propanoate (150 mg, 0.34 mmol) obtained in Example 11 and sodium carbonate (180 mg, 1.7 mmol) by a similar procedure to that described in Example 3. mp: 80–82° C.

$^1$H NMR (CDCl$_3$): δ 7.91 (d, J=7.50 Hz, 1H), 7.43 (t, J=7.50 Hz, 1H), 7.16 (d, J=8.40 Hz, 2H), 7.06 (t, J=7.50 Hz, 1H), 6.88 (d, J=7.50 Hz, 1H), 6.84 (d, J=8.40 Hz, 2H), 4.20 (t, J=5.30 Hz, 2H), 4.04 (dd, J=7.25 and 4.25 Hz, 1H), 3.91 (t, J=5.30 Hz, 2H), 3.70–3.35 (m, 2H), 3.08 (dd, J=14.11 and 4.25 Hz, 1H), 2.93 (dd, J=14.11 and 7.25 Hz, 1H), 1.75 (s, 6H), 1.17 (t, J=6.95 Hz, 3H).

EXAMPLE-13

(±) Methyl 2-ethoxy-3-[4-[[4-oxo-3,4-dihydro-1,3-benzoxazin-2-yl]methoxy]phenyl]propanoate

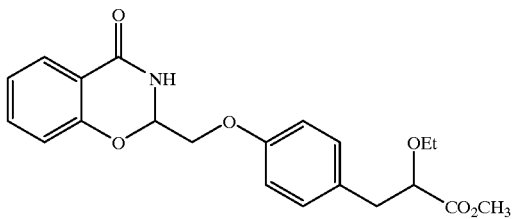

To a stirred solution of polyphosphonate ethyl ester (PPE) (3.46 g, 8.0 mmol) in chloroform (10 mL) was added salicylamide (548 mg, 4.0 mmol) followed by addition of a solution of (±)-Methyl 2-ethoxy-3-[4-[(2,2diethoxy)ethoxy] phenyl]propanoate (1.28 g, 4.4 mmol) obtained in preparation 2, in chloroform (10 mL) dropwise at 25–30° C. The reaction mixture was immersed in a preheated oil bath at 70° C. and refluxed 12 h. The reaction mixture was cooled to room temperature and CHCl$_3$ was removed under reduced pressure. The resultant residue was neutralised (pH=7.0) with saturated aqueous NaHCO$_3$ solution and extracted with ethyl acetate (3×20 mL). The combined organic extracts were washed with brine, dried over anhydrous Na$_2$SO$_4$ and concentrated. The crude compound was chromatographed on silica gel using a gradient of 5–25% of ethyl acetate in pet ether as eluent to afford the title compound (1.15 g, 72%) as a pale yellow liquid.

$^1$H NMR (CDCl$_3$): δ 7.97 (d, J=7.75 Hz, 1H), 7.50 (t, J=8.50 Hz, 1H), 7.19 (d, J=8.62 Hz, 2H), 7.15 (t, J=7.50 Hz,

1H), 7.02 (d, J=8.50 Hz, 1H), 6.87 (d, J=8.62 Hz, 2H), 5.69 (t, J=4.95 Hz, 1H), 4.39 (dd, J=9.64, 4.19 Hz, 1H), 4.30–3.90 (m, 2H), 3.72 (s, 3H), 3.71–3.50 (m, 1H), 3.45–3.21 (m, 1H), 2.97 (d, J=6.96 Hz, 2H), 1.17 (t, J=7.05 Hz, 3H).

EXAMPLE-14

(±)-2-Ethoxy-3-4-[[4-oxo-3,4-dihydro 1,3-benzoxazin-2-yl]methoxy]phenyl]propanoico acid

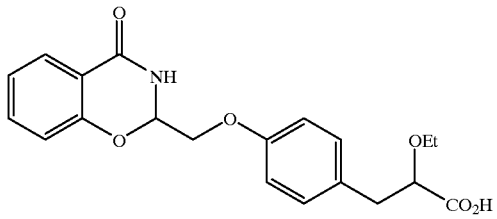

The title compound (300 mg, 75/o) was obtained from (±)-methyl 2-ethoxy-3-[4-[[4-oxo-3,4-dihydro-1,3-benzoxazin-2-yl]ethoxy]phenyl]propanoate (432 mg, 1.08 mmol) obtained in Example 13, and sodium carbonate (318 mg, 3.0 mmol) by a similar procedure to that described in Example 3. mp: 126–128° C.

¹H NMR (CDCl₃): δ 7.96 (d, J=7.80 Hz, 1H), 7.50 (t, J=7.80 Hz, 1H), 7.19 (d, J=8.50 Hz, 2H), 7.12 (t, J=7.80 Hz, 1H), 7.01 (d, J=7.80 Hz, 1H), 6.84 (d, J=8.50 Hz, 2H), 5.65 (t, J=5.35 Hz, 1H), 4.35 (dd, J=9.90 and 4.25 Hz, 1H), 4.16 (dd, J=9.60 and 6.60 Hz, 1H), 4.07 (t, J=5.80 Hz, 1H), 3.70–3.52 (m, 1H), 3.52–3.40 (m, 1H), 3.20–2.90 (m, 2H), 1.20 (t, J=7.05 Hz, 3H).

EXAMPLE-15

(±)-Methyl 2-ethoxy-3-[4-[[4-oxo-1,2,3,4-tetrahydro-2quinazolinyl]methoxy]phenyl]propanoate

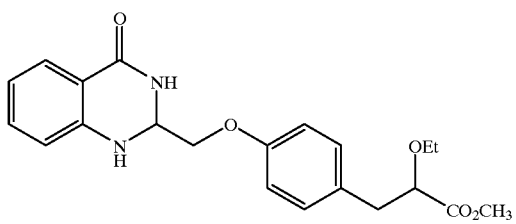

The title compound (900 mg, 62%) was obtained as a liquid from anthranilamide (500 mg, 3.67 mmol), (±)-methyl 2-ethoxy-3-[4-[(2,2-diethoxy)ethoxy]phenyl] propanoate (1.43 g, 4.0 mmol) obtained in preparation 2 and polyphosphonate ethyl ester (3.18 g, 7.35 mmol) by a similar procedure to that described in Example 13.

¹H NMR (CDCl₃): δ 7.91 (d, J=7.50 Hz, 1H), 7.36 (t, J=7.50 Hz, 1H), 7.19 (d, J=8.40 Hz, 2H), 6.90 (t, J=7.50 Hz, 1H), 6.85 (d, J=8.40 Hz, 2H), 6.72 (d, J=7.50 Hz, 1H), 6.37 (bs, 1H, D₂O exchangeable), 5.23 (t, J=5.00 Hz, 1H), 4.40–4.10 (m, 2H), 4.10–3.90 (m, 1H), 3.74 (s, 3H), 3.70–3.52 (m, 1H), 3.48–3.22 (m, 1H), 2.99 (d, J=6.22 Hz, 2H), 1.19 (t, J=6.95 Hz, 3H).

EXAMPLE-16

(±)-2-Ethoxy-3-[4-[[4-oxo-1,2,3,4-tetrahydro-2-quinazolinyl]methoxy]phenyl]propanoic acid

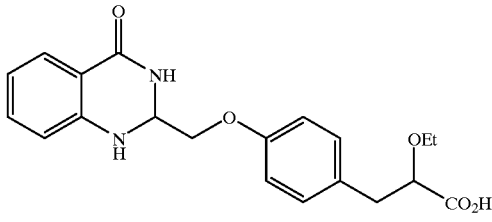

The title compound (360 mg, 69%) was obtained from (±)-methyl 2-ethoxy-3-[4-[[4-oxo-1,2,3,4-tetrahydro-2-quinazolinyl]methoxy]phenyl]propanoate (560 mg, 1.4 mmol) obtained in Example 15, and sodium carbonate (750 mg, 7.0 mmol) by a similar procedure to that described in Example 3: mp 173° C.

¹H NMR (CDCl₃+DMSO): δ 7.79 (d, J=7.50 Hz, 1H), 7.44 (bs, 1H, D₂O exchangeable), 7.27 (t, J=7.50 Hz, 1H), 7.17 (d, J=8.30 Hz, 2H), 6.81–6.69 (m, 4H), 5.87 (bs, 1H, D₂O exchangeable ), 5.12 (t, J=5.10 Hz, 1H), 4.20–3.95 (m, 2H), 3.92 (dd, J=7.80, 4.89 Hz, 1H), 3.72–3.50 (m, 1H), 3.40–3.20 (m, 1H), 3.10–2.80 (m, 2H), 1.14 (t, J=6.95 Hz, 3H).

EXAMPLE-17

(±)-Methyl-2-ethoy-3-[4-[[6-chloro-4-oxo-, 1,2, 3,4-tetrahydro-2-quinazolinyl]methoxy]phenyl]propanoate

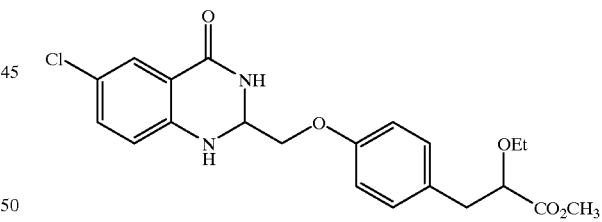

The title compound (640 mg, 50%) was obtained as a liquid from 5-chloroanthranilamide (500 mg, 2.93 nmmol), (±)-methyl 2-ethoxy-3-[4-[(2,2-diethoxy)ethoxy]phenyl] propanoate (1.41 g, 3.22 mmol) obtained in preparation 2 and polyphosphonate ethyl ester (2.53 g, 5.86 mmol) by a similar procedure to that described in Example 13.

¹H NMR (CDCl₃): δ 7.83 (d, J=2.26 Hz, 1H), 7.23 (t, J=8.60 Hz, 1H), 7.13 (d, J=8.40 Hz, 2H), 6.78 (d, J=8.40 Hz, 2H), 6.63 (d, J=8.60 Hz, 1H), 5.17 (t, J=4.70 Hz, 1H), 4.75 (bs, 1H, D₂O exchangeable), 4.11 (t, J=6.60 Hz, 1H), 3.99 (q, J=4.70 Hz, 2H), 3.70 (s, 3H), 3.70–3.50 (m, 1H), 3.40–3.20 (m, 1H), 2.95 (d, J=6.60 Hz, 2H), 1.14 (t, J=6.95 Hz, 3H).

EXAMPLE-18

(±)-2-Ethoxy-3-[4-[[6-chloro-4-oxo-1,2,3,4-tetrahydro-2-quinazolinyl]methoxy]phenyl] propanoic acid

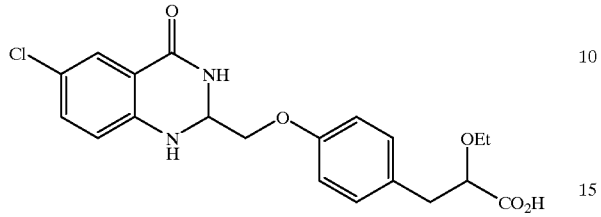

The title compound (140 mg, 73%) was obtained from (±)-methyl 2-ethoxy-3-[4-[[6-chloro-4-oxo-1,2,3,4-tetrahydro-2-quinazolinyl]methoxy]phenyl]propanoate (200 mg, 0.46 mmol) obtained in Example 17 and sodium carbonate (245 mg, 2.31 mmol) by a similar procedure to that described in Example 3: mp: 156–158° C.

$^1$H NMR (CDCl3): δ 8.19 (s, 1H), 7.25–7.05 (m, 1H), 7.13 (d, J=8.30 Hz, 2H), 7.03 (bs, 1H, D$_2$O exchangeable), 6.85–6.70 (m, 1H), 6.78 (d, J=8.30 Hz, 2H), 5.02 (t, J=4.90 Hz, 1H), 4.10–3.80 (m, 3H), 3.70–3.45 (m, 1H), 3.45–3.20 (m, 1H), 3.0–2.70 (m, 2H), 1.08 (t, J=6.95 Hz, 3H).

EXAMPLE-19

(±)-Methyl 2-ethoxy-3-[4-[[3-methyl-4-oxo-1,2,3,4-tetrahydro-2-quinazolinyl]methoxyl]phenyl] propanoate

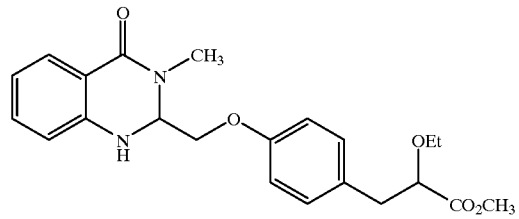

The title compound (870 mg, 41%) was obtained as a liquid from N-methyl anthranilamide (765 mg, 5.1 mmol), (±)-methyl 2ethoxy-3-[4-[(2,2-diethoxy)ethoxy]phenyl] propanoate obtained in preparation 2 (2.0 g, 5.6 mmol) and polyphosphonate ethyl ester (4.40 g, 10.2 mmol) by a similar procedure to that described in Example 13: mp 138–140° C.

$^1$H NMR (CDCl$_3$): δ 7.91 (d, J=7.60 Hz, 1H), 7.27 (t, J=7.60 Hz, 1H), 7.13 (d, J=8.50 Hz, 2H), 6.86 (t, J=7.60 Hz, 1H), 6.75 (d, J=8.50 Hz, 2H), 6.65 (d, J=7.60 Hz, 1H), 4.94 (dd, J=8.50 and 3.25 Hz, 1H), 4.82 (bs, 1H, D$_2$O exchangeable), 4.11 (t, J=8.80 Hz, 1H), 4.02–3.90 (m, 2H), 3.70 (s, 3H), 3.70–3.48 (m, 1H), 3.42–3.25 (m, 1H), 3,20 (s, 3H), 2.94 (d, J=6.13 Hz, 2H), 1.15 (t, J=7.01 Hz, 3H1).

EXAMPLE-20

(±)-2-Ethoxy-3-[4-[[3-methyl-4-oxo-1,2,3,4-tetrahydro-2-quinazolinyl]methoxy]phenyl] propanoic acid

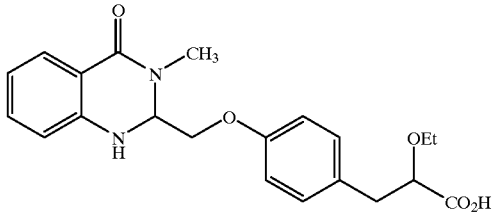

The title compound (64 mg, 72%) was obtained as a liquid from (±)-methyl 2-ethoxy-3-[4-[[3-methyl-4-oxo-1,2,3,4-tetahydro-2-quinazolinyl]methoxy]phenyl]propanoate obtained in Example 19 (100 mg, 0.23 mmol) and sodium carbonate (124 mg, 1.16 mmol) by a similar procedure to that described in Example 3:

$^1$H NMR (CDCl$_3$): δ 7.90 (d, J=7.50 Hz, 1H), 7.26 (t, J=7.50 Hz, 1H), 7.14 (d J=8.40 Hz, 2H), 6.86 (t, J=7.50 Hz, 1H), 6.75 (d, J=8.40 Hz, 2H), 6.65 (d, J=7.50 Hz, 1H), 4.95 (dd, J=8.65 and 3.85 Hz, 1H), 4.20–3.90 (m, 3H), 3.75–3.35 (m, 2H), 3.20 (s, 3H, 3.15–2.80 (m, 2H), 1.18 (t, J=7.0 Hz, 3H).

EXAMPLE-21

(±)-Methyl 2-ethoxy-3-[4-[[3-methyl-4-oxo-3,4-dihydro-1,3-benzoxazin-2yl]methoxy]phenyl] propanoate

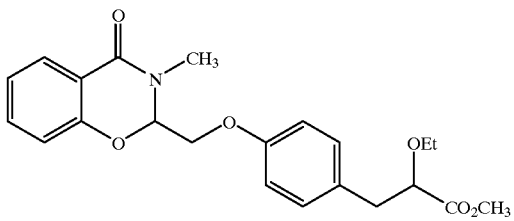

The title compound (735 mg, 60%) was obtained as a gummy mass from N-methyl salicylamide (450 mg, 3.0 mmol), (±)-methyl 2-ethoxy-3-[4-[(2,2-diethoxy)ethoxy] phenyl]propanoate obtained in preparation 2 (1.16 g, 3.3 mmol) and polyphosphonate ethyl ester (2.59 g, 6.0 mmol) by a similar procedure to that described in Example 13.

$^1$H NMR (CDCl3): δ 7.93 (d, J=7.50 Hz, 1H), 7.42 (t, J=7.50 Hz, 1H), 7.12 (d, J=8.40 Hz, 2H), 7.09 (t, J=7.50 Hz, 1H), 6.94 (d, J=7.50 Hz, 1H), 6.75 (d, J=8.40 Hz, 2H), 5.62 (t, J=5.50 Hz, 1H), 4.25 (dd, J=10.25 and 6.25 Hz, 1H), 4.12 (dd, J=10.25 and 5.25 Hz, 1H), 3.96 (t, J=6.50 Hz, 1H), 3.70 (s, 3H), 3.70–3.50 (m, 1H), 3.40–3.15 (m, 1H), 3.22 (s, 3H), 2.93 (d, J=6.50 Hz, 2H), 1.14 (t, J=7.05 Hz, 3H).

EXAMPLE-22

(±)-2-Ethoxy-3-[4-[[3-methyl-4-oxo-3,4-dihydro-1,3-benzoxazin-2-yl]methoxy]phenyl]propanoic acid

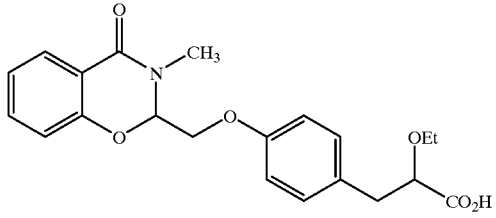

The title compound (325 mg, 75%) was obtained as a liquid from (±)-methyl 2-ethoxy-3-[4-[[3-methyl-4-oxo-3,4-dihydro-1,3-benzoxazin-2-yl]methoxy]phenyl]propanoate (472 mg, 1.18 mmol) obtained in Example 21 and sodium carbonate (362 mg, 3.42 mmol) by a similar procedure to that described in Example 3.

$^1$H NMR (CDCl$_3$): δ 7.90 (d, J=7.50 Hz, 1H), 7.40 (t, J=7.50 Hz, 1H), 7.10 (d, J=8.40 Hz, 2H), 7.05 (t, J=7.50 Hz, 1H), 6.90 (d, J=7.50 Hz, 1H), 6.75 (d, J=8.40 Hz, 2H), 5.30 (t, J=5.50 Hz, 1H), 4.20 (dd, J=9.75, 5.95 Hz, 1H), 4.10 (dd, J=9.75 and 4.95 Hz, 1H), 4.01 (t, J=6.40 Hz, 1H), 3.72–3.52 (m, 1H), 3.42–3.20 (m, 1H), 3.20 (s, 3H), 3.05–2.80 (m, 2H,), 1.15 (t, J=6.95 Hz, 3H).

EXAMPLE-23

(±)-Methyl 2-ethoxy-3-[4-[[3-ethyl-4-oxo-1,2,3,4-tetrahydro-2-quinazolinyl]methoxy]phenyl]propanoate

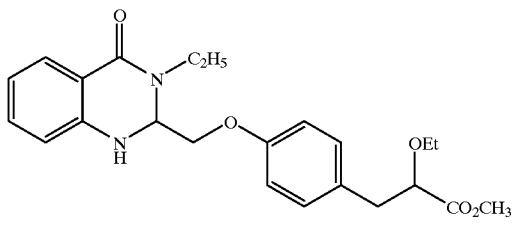

The title compound (1.18 g, 54%) was obtained as a colorless liquid from N-ethyl-anthranilamide (840 mg, 5.1 mmol), (±)-methyl 2-ethoxy-3-[4-[(2,2-diethoxy)ethoxy]phenyl]propanoate obtained in preparation 2 (2.0 g, 5.6 mmol) and polyphosphonate ethyl ester (4.40 g, 10.2 mmol) by a similar procedure to that described in Example 13.

$^1$H NMR (CDCl3): δ 7.89 (d, J=7.50 Hz, 1H), 7.25 (t, J=7.50 Hz, 1H), 7.11 (d, J=8.40 Hz, 2H), 6.83 (t, J=7.50 Hz, 1H), 6.73 (d, J=8.40 Hz, 2H), 6.63 (d, J=7.50 Hz, 1H), 4.95 (dd, J=8.72 and 3.32 Hz, 1H), 4.40–3.80 (m, 4H), 3.68 (s, 3H), 3.62–3.40 (m, 1H), 3.40–3.22 (m, 1H), 3.22–3.02 (m, 1H), 2.93 (d, J=6.22 Hz, 2H), 1.28 (t, J=7.15 Hz, 3H), 1.14 (t, J=6.95 Hz, 3H).

EXAMPLE-24

(±)-2-Ethoxy-3-[4-[[3-ethyl-4-oxo-1,2,3,4-tetrahydro-2-quinazolinyl]methoxy]phenyl]propanoic acid

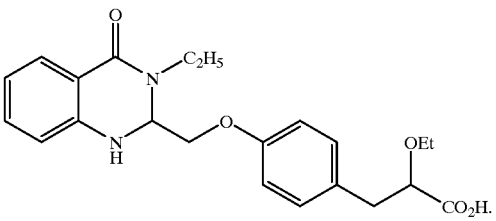

The title compound (324 mg, 81%) was obtained as a liquid from (±)-methyl 2-ethoxy-3-[4-[[3-ethyl-4-oxo-1,2,3,4-tetrahydro-2-quinazolnyl]methoxy]phenyl]propanoate obtained in Example 23 (520 mg, 1.22 mmol) and sodium carbonate (647 mg, 6.1 mmol) by a similar procedure to that described in Example 3.

$^1$H NMR (CDCl$_3$): δ 7.85 (d, J=7.50 Hz, 1H), 7.20 (t, J=7.50 Hz, 1H), 7.10 (d, J=8.40 Hz, 2H), 6.80 (t, J=7.50 Hz, 1H), 6.70 (d, J=8.40 Hz, 2H), 6.60 (d, J=7.40 Hz, 1H), 4.90 (dd, J=8.50 and 3.25 Hz, 1H), 4.40–3.80 (m, 4H), 3.70–3.40 (m, 1H), 3.40–3.20 (m, 3.20–3.00 (m, 1H), 2.90 (d, J=6.20 Hz, 2H), 1.25 (t, J=7.10 Hz, 3H), 1.14 (t, J=7.00 Hz, 3H).

EXAMPLE-25

(±)-Methyl 2-ethoxy-3-[4-[[1,3-dimethyl-4-oxo-1,2,3,4-tetrahydro-2-quinazolinyl]methoiy]phenyl]propanoate

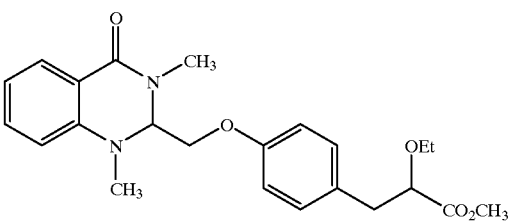

The title compound (400 mg, 54%) was obtained as a liquid from N,N$^1$-dimethyl-anthranilamide (295 mg, 1.79 mmol), (±)-methyl 2-ethoxy-3-[4-[(2,2-diethoxy)ethoxy]phenyl]propanoate (700 mg, 1.97 mmol), obtained in preparation 2 and polyphosphonate ethylester (1.54 g, 3.58 mmol) by a similar procedure to that described in Example 13.

$^1$H NMR (CDCl$_3$): δ 7.92 (d, J=7.50 Hz, 11), 7.35 (t, J=8.30 Hz, 1H), 7.08 (d, J=8.40 Hz, 2H), 6.82 (t, J=7.50 Hz, 1H), 6.67 (d, J=8.40 Hz, 2H), 6.61 (d, J=8.32 Hz, 1H), 4.85 (d, J=5.80 Hz, 1H), 4.29–3.90 (m, 3H), 3.70–3.50 (m, 1H), 3.67 (s, 3H), 3.40–3.20 (m, 1H), 3.22 (s, 3H), 3.10 (s, 3H), 2.90 (d, J=6.55 Hz, 2H), 1.12 (t, J=6. 97 Hz, 3H).

EXAMPLE-26

(±)-2-Ethoxy-3-[4-[[1,3-dimethyl-4-oxo-1,2,3,4-tetrahydro-2-quinazolinyl]methoxyl]phenyl]propanoic acid

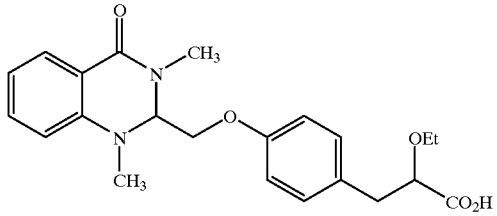

The title compound (103 mg, 72%) was obtained as a liquid from (±)-methyl 2-ethoxy-3-[4-[[1,3-dimethyl-4-oxo-1,2,3,4-tetrahydro-2-quinazolinyl]methoxy]phenyl]propanoate (150 mg, 0.36 mmol), obtained in Example 25 and sodium carbonate (192 mg, 1.81 mmol) by a similar procedure to that described in Example 3.

$^1$H NMR (CDCl$_3$): δ 7.90 (d, J=7.50 Hz, 1H), 7.30 (t, J=8.30 Hz, 1H), 7.05 (d, J=8.40 Hz, 2H), 6.80 (t, J=7.50 Hz, 1H), 6.60 (d, J=8.40 Hz, 2H), 6.60 (d, J=8.30 Hz, 1H), 4.80 (t, J=5.80 Hz, 1H), 4.30–3.90 (m, 3H), 3.70–3.50 (m, 1H), 3.40–3.20 (m, 1H), 3.20 (s, 3H), 3.10 (s, 3H,), 2.90 (d, J=6.50 Hz, 2H), 1.14 (t, J=7.0 Hz, 3H).

EXAMPLE-27

(±)-Methyl 2-phenoxy-3-[4-[[4-oxo-1,2,3,4-tetrahydro-2-quinazolinyl]methoxy]phenyl]propanoate

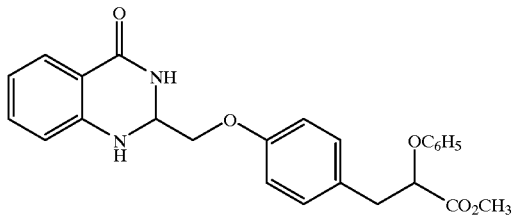

The title compound (395 mg, 58%) was obtained as a liquid from anthranilamide (200 mg, 1.47 mmol), (±)-methyl 2-phenoxy-3-[4-[(2,2-diethoxy)ethoxy]phenyl]propanoate (650 mg, 1.61 mmol) obtained in preparation 4 and polyphosphonate ethyl ester (1.27 g, 2.94 mmol) by a similar procedure to that described in Example 13.

$^1$H NMR (CDCl$_3$): δ 7.90 (d, J=7.75 Hz, 1H), 7.34 (t, J=7.75 Hz, 1H), 7.35–7.15 (m, 3H), 7.23 (d, J=8.40 Hz, 2H), 6.96 (t, J=7.80 Hz, 1H), 6.90–6.80 (m, 2H), 6.83 (d, J=8.40 Hz, 2H), 6.69 (d, J=7.80 Hz, 1H), 6.55 (bs, 1H, D$_2$O exchangeable), 5.20 (t, J=6.50 Hz, 4.76 (t, J=6.40 Hz, 1H), 4.65 (bs, 1H, D$_2$O exchangeable), 4.20 (dd, J=8.90 and 7.15 Hz, 1H), 4.01 (dd, J=8.90 and 5.15 Hz, 1H), 3.72 (s, 3H), 3.19 (d, J=6.40 Hz, 2H).

EXAMPLE-28

(±)-2-Phenoxy-3-[4-[[4-oxo-1,2,3,4-tetrahydro-2-quinazolinyl]methoxy] phenyl]propanoic acid

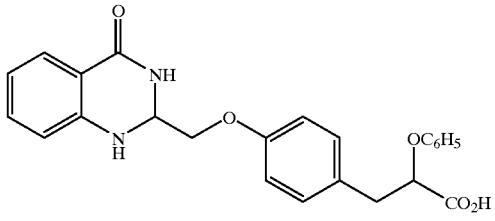

The title compound (488 mg, 86%) was obtained as a white solid from (±)-methyl 2-phenoxy-3-[4-[[4-oxo-1,2,3,4-tetrahydro-2-quinazolinyl]methoxy]phenyl]propanoate (611 mg, 1.14 mmol) obtained in Example 27 and sodium carbonate (726 mg, 6.84 mmol) by a similar procedure to that described in Example 3, m.p: 78–80° C.

$^1$H NMR (CDCl$_3$): δ 7.94 (bs, 1H, D$_2$O exchangeable), 7.83 (d, J=7.38 Hz, 1H), 7.40–7.15 (m, 5H), 6.98 (t, J=7.38 Hz, 1H), 6.92 (d, J=8.30 Hz, 2H), 6.84 (t, J=8.40 Hz, 1H), 6.72 (d, J=8.30 Hz, 2H), 6.63 (d, J=8.40 Hz, 1H), 4.98 (t, J=5.10 Hz, 1H), 4.89 (t, J=5.30 Hz, 1H), 3.94 (dd, J=8.90 and 7.15 Hz, 1H), 3.70 (dd, J=8.90 and 4.05 Hz, 1H), (d, J=5.30 Hz, 2H).

EXAMPLE-29

(±)-Methyl 2-phenoxy-3-[4-[[6-chloro-4-oxo-1,2,3,4-tetrahydro-2-quinazolinyl]methoxy]phenyl]propanoate

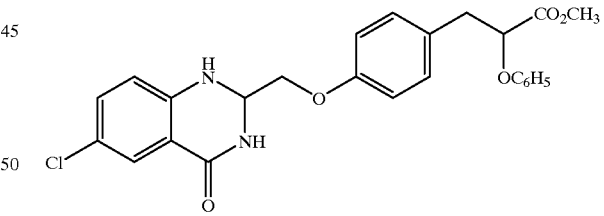

The title compound (488 mg, 47%) was obtained as a liquid from 5-chloroanthranilamide (368 mg, 2.15 mmol), (±)-methyl 2-phenoxy-3-[4-[(2,2-diethoxy) ethoxy]phenyl]propanoate (954 mg, 2.37 mmol) obtained in preparation 4 and polyphosphonate ethyl ether (1.864 mg, 4.3 mmol) by a similar procedure to that described in Example 13.

$^1$H NMR (CDCl$_3$): δ 7.84 (s, 1H), 7.31–7.19 (m, 5H), 7.01–6.91 (m, 1H), 6.85–6.79 (m, 4H), 6.61 (d, J=8.62 Hz, 1H), 5.16 (bs, 11H), 4.75 (t, J=6.22 Hz, 2H), 4.19–4.06 (m, 1H), 3.71 (s, 3H), 3.18 (d, J=6.55 Hz, 2H).

EXAMPLE-30

(±)-2-Phenoxy-3-[4-[[6-chloro-4-oxo-1,2,3,4-tetrahydro-2-quinazolinyl]methoxy]phenyl]propanoic acid

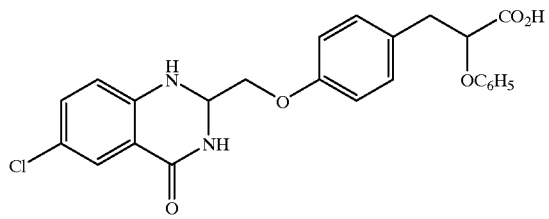

The title compound (300 mg, 65%) was obtained from (±) methyl 2-phenoxy-3-[4-[[6-chloro-4-oxo-1,2,3,4-tetrahydro-2-quinazolinyl]methoxy]phenyl]propanoate (488 mg, 1.01 mmol) obtained in Example 29 and sodium carbonate (530 mg, 5.08 mmol) by a similar procedure to that described in Example 3: mp: 54–56° C.

$^1$H NMR (CDCl$_3$): δ 7.80 (s, 1H), 7.31–7.18 (m, 5H), 6.99 (d, J=7.47 Hz, 1H), 6.90 (d, J=8.3 Hz, 2H), 6.73 (d, J=8.54 Hz, 2H), 6.58 (d, J=7.88 Hz, 1H), 5.02 (bs, 1H), 4.89 (t, J=4.98 Hz, 1H), 4.01–3.91 (m, 1H), 3.78–3.66 (m, 1H), 3.25 (d, J=5.30 Hz, 2H).

EXAMPLE-31

(±)-Ethyl 2-ethoxy-3-[4-[2-[6-nitro-4-oxo-3,3,4-dihydro-1,3-benzoxazin-3-yl]ethoxy]phenyl]propanoate

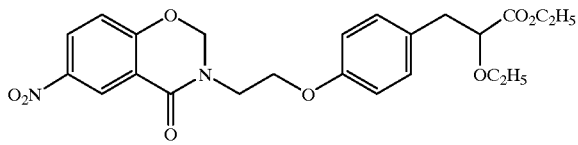

The title compound (160 mg, 41.5%) was obtained as a liquid from 3-(2-hydroxyethyl)-6-nitro-4-oxo-3,4-dihydro-1,3-benzoxazine (200 mg, 0.84 mmol), (±)-ethyl 2-ethoxy-3-(4-hydroxyphenyl)propanoate (200 mg, 0.84 mmol), triphenylphosphine (330 mg, 1.26 mol) and diisopropyldiazodicarboxylate (255 mg, 1.26 mmol) by a similar procedure to that described in Example 5.

$^1$H NMR (CDCl$_3$): δ 8.82 (s, 1H), 8.35–8.26 (m, 11H), 7.19–7.04 (m, 3H), 6.77 (d, J=8.54 Hz, 2H), 5.47 (s, 2H), 4.28–4.10 (m, 5H), 3.96 (t, J=4.77 Hz, 2H), 3.68–3.50 (m, 1H), 3.40–3.22 (m, 1H), 2.92 (d, J=6.55 Hz, 2H), 1.35–1.09 (m, 6H).

EXAMPLE-32

(±)-2-Ethoxy-3-[4-[2-[6-nitro-4-oxo-3,4-dihydro-1,3-benzoxazin-3-yl]ethoxy]pheyl]propanoic acid

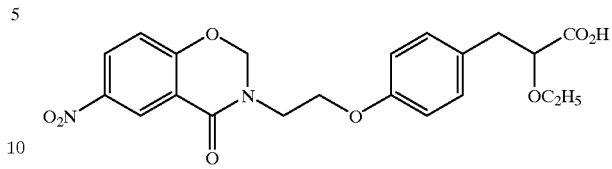

The title compound (226 mg, 63%) was obtained from (±)thyl 2-ethoxy-3-[4-[2-[6-nitro-4-oxo-3,4-dihydro-1,3-benzoxazin-3-yl]ethoxy]phenyl]propanoate (339 mg, 0.74 mmol) obtained in Example 31 and sodium carbonate (392 mg, 3.70 mmol) by a similar procedure to that described in Example 3: mp: 110° C.

$^1$H NMR (CDCl$_3$): δ 8.87 (s, 1H), 8.40–8.31 (m, 1H), 7.31–7.10 (m, 3H), 6.81 (d, J=8.40 Hz, 2H), 5.50 (s, 2H), 4.21 (t, J=4.56 Hz, 2H), 4.11–3.98 (m, 3H), 3.70–3.39 (m, 2H), 3.16–2.90 (m, 2H), 1.19 (t, J=6.98 Hz, 3H).

EXAMPLE-33

(±)-Ethyl 2-ethoxy-3-[4-[2-[6-acetyl-4-oxo-3,4-dihydro-1,3-benzoxazin-3-yl]ethoxy]phenyl]propanoate

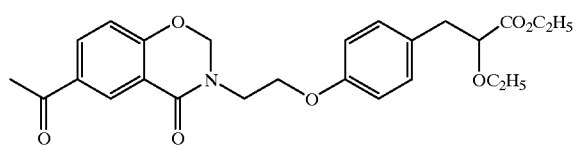

The title compound (168 mg, 43.4%) was obtained as a liquid from 3-(2-hydroxy-ethyl)-6-acetyl-4-oxo-3,4-dihydro-1,3-benzoxazine (200 mg, 0.85 mmol), (±)-ethyl 2-ethoxy-3-(4-hydroxyphenyl)propanoate (202 mg, 0.85 mmol), triphenylphosphine (334 mg, 1.27 mmol) and diisopropyldiazodicarboxylate (258 mg, 1.27 mmol) by a similar procedure to that described in Example 5.

$^1$H NMR (CDCl$_3$): δ 8.51 (s, 1H), 8.08 (d, J=6.41 Hz, 1H), 7.13 (d, J=8.63 Hz, 2H), 7.02 (d, J=8.72 Hz, 1H), 6.77 (d, J=8.63 Hz, 2H), 5.41 (s, 2H), 4.28–4.08 (m, 5H), 3.93 (t, J=4.86 Hz, 2H), 3.65–3.49 (m, 1H), 3.41–3.21 (m, 1H), 2.92 (d, J=6.64 Hz, 2H), 2.59 (s, 3H), 1.39–1.10 (m, 6H).

EXAMPLE-34

(±)-2-Ethoxy-3-[4-[2-[6-acetyl-4-oxo-3,4-dihydro-1,3-benzoxazin-3-yl]ethoxy]phenyl]propanoic acid

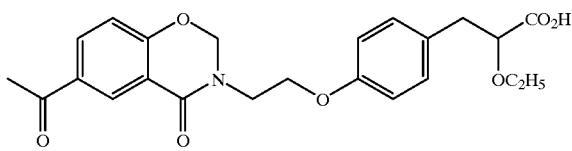

The title compound (120 mg, 84%) was obtained as a liquid from (±)-ethyl 2-ethoxy-3-[4-[2-[6-acetyl-4-oxo-3,4-dihydro-1,3-benzoxazin-3-yl]ethoxy]phenyl]propanoate (152 mg, 0.33 mmol) obtained in Example 33 and sodium carbonate (177 mg, 1.67 mmol) by a similar procedure to that described in Example 3.

$^1$H NMR (CDC$_{13}$): δ 8.53 (s, 1H), 8.11 (d, J=6.50 Hz, 1H), 7.16 (d, J=8.40 Hz, 2H), 7.04 (d, J=8.72 Hz, 1H), 6.80 (d, J=8.40 Hz, 2H), 5.40 (s, 2H), 4.16 (t, J=2H), 3.91–4.04 (m, 3H), 3.70–3.51 (m, 1), 3.50–3.31 (m, 1H), 3.12–2,88 (m, 2H), 2,61 (s, 3H), 1.16 (t, J=6.84 Hz, 3H).

The compounds of the present invention lowered random blood sugar level, triglyceride, total cholesterol, LDL, VLDL and increased HDL. This was demonstrated by in vitro as well as in vivo animal experiments.

Demonstration of Efficacy of Compounds

A) In vitro a) Determination of hPPARα activity

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene. 1992. 118: 137–141; Superfect Trnsfection Reagent Handbook. February, 1997. Qiagen, Germany).

b) Determination of hPPARγ activity

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 μM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992. 118:137–141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| Example 3 | 50 μM | 7 | 1 μM | 11 | c) Determination of HMG CoA reductase inhibition activity

Liver microsome bound reductase was prepared from 2% cholestramine fed rats at mid-dark cycle. Spectrophotometric assays were carried out in 100 mM KH$_2$PO$_4$, 4 mM DTT, 0.2 mM NADPH, 0.3 mM HMG CoA and 125 μg of liver microsomal enzyme. Total reaction mixture volume was kept as 1 ml. Reaction was started by addition of HMG CoA. Reaction mxue was incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450–1461). The test compounds inhibited the HMG CoA reductase enzyme.

B) In vivo a) Efficacy in genetic models

Mutation in colonies of laboratory animals and different sensitivities to dietary. regimens have made the development of animal models with non-insulin dependent diabetes and hyperlipidemia associated with obesity and insulin resistance possible. Genetic models such as db/db and ob/ob (Diabetes, (1982) 31 (1):1–6) mice and zucker fa/fa rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.001 mg to 30 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 μl) through orbital sinus, using heparinised capillary in tubes containing EDTA which was centrifuged to obtain plasma The plasma glucose and triglyceride levels were measured spectrometrically, by glucose oxidase and glycerol-3-PO4 oxidase/peroxidase enzyme (Dr. Reddy's Lab. Diagnostic Division Kits, Hyderabad, India) methods respectively.

The blood sugar and triglycerides lowering activities of the test compound was calculated according to the formula described below.

No adverse effects were observed for any of the mentioned compounds of invention in the above test.

| Compound | Dose (mg/kg) | Reduction in Blood Glucose Level (%) | Triglyceride Lowering (%) |
|---|---|---|---|
| Example 14 | 3 | 55 | 46 |
| Example 16 | 3 | 18 | 13 |
| Example 19 | 3 | 31 | 62 |

The ob/ob mice were obtained at 5 weeks of age from Bomholtgard, Demark and were used at 8 weeks of age. Zucker fafa fatty rats were obtained from IffaCredo, France at 10 weeks of age and were used at 13 weeks of age. The animals were maintained under 12 hour light and dark cycle at 25±1° C. Animals were given standard laboratory chow (NIN, Hyderabad, India) and water, ad libitum (Fujiwara, T., Yoshioka, S., Yoshioka, T., Ushiyama, I and Horikoshi, H.

Characterization of new oral antidiabetic agent CS-045. Studies in KK and ob/ob mice and Zucker fatty rats. Diabetes. 1988. 37: 1549–1558).

The test compounds were administered at 0.1 to 30 mg/kg/day dose for 9 days. The control animals received the vehicle (0.25% carboxymethylcellulose, dose 10 ml/kg) through oral gavage.

The blood samples were collected in fed state 1 hour after drug administration on 0 and 9 day of treatment The blood was collected from the retro-orbital sinus through heparinised capillary in EDTA containing tubes. After centfugation, plasma sample was separated for triglyceride, glucose, free fatty acid, total cholesterol and insulin estimations. Measurement of plasma triglyceride, glucose, total cholesterol were done using commercial kits (Dr. Reddy's Laboratory, Diagnostic Division, Hyderabad, India). The plasma free fatty acid was measured using a commercial kit form Boehringer Mannheim, Germany. The plasma insulin was measured using a RIA kit (BARC, India). The reduction of various parameters examined are calculated according to the formula.

In ob/ob mice oral glucose tolerance test was performed after 9 days treatment. Mice were fasted for 5 hrs and challenged with 3 gm/kg of glucose orally. The blood samples were collected at 0, 15, 30, 60 and 120 min for estimation of plasma glucose levels.

The experimental results from the db/db mice, ob/ob mice, Zucker fa/fa rats suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

b) Cholesterol lowering activity in hypercholesterolemic rat models:

Male Sprague Dawley rats (NIN stock) were bred in DRF animal house. Animals were maintained under 12 hour light and dark cycle at 25±1° C. Rats of 180–200 gram body weight range were used for the experiment Animals were made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74: 215–225).

The test compounds were administered orally at a dose 0.1 to 30 mg/kg/day for 3 days. Control group was treated with vehicle alone (0.25% Carboxymethylcellulose; dose 10 ml/kg).

The blood samples were collected in fed state 1 hour after drug administration on 0 and 3 day of compound treatment The blood was collected from the retro-orbital sinus through heparinised capillary in EDTA containing tubes. After centrifugation, plasma sample was separated for total cholesterol, HDL and triglyceride estimations. Measurement 2 of plasma triglyceride, total cholesterol and HDL were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

| Compound | Dose Mg/kg | Triglyceride (%)↓ | Total Cholesterol (%)↓ | HDL↑ (%) | LDL↓ (%) | VLDL↓ (%) |
| --- | --- | --- | --- | --- | --- | --- |
| Example 4 | 3 mg/kg | 61 | 64 | 256 | 76 | 67 |
| Example 3 | 0.3 mg/kg | 62 | 64 | 110 | 74 | 50 | c) Plasma triglyceride and total cholesterol lowering activity in Swiss albino mice and Guinea Digs Male Swiss albino mice (SAM) and male Guinea pigs were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20–25 g body weight range and Guinea pigs of 500–700g body weight range were used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds were administered orally to Swiss albino mice at 0.3 to 30 mg/kg/day dose for 6 days. Control mice were treated with vehicle (0.25% Carboxymethylcellulose; dose 10 ml/kg). The test compounds were administered orally to Guinea pigs at 0.3 to 30 mg/kg/day dose for 6 days. Control animals were treated with vehicle (0.25% Carboxymethylcellulose; dose 5 ml/kg).

The blood samples were collected in fed state 1 hour after drug administration on 0 and 6 day of treatment. The blood was collected from the retro-orbital sinus through heparinised capillary in EDTA containing tubes. After centrifigation, plasma sample was separated for triglyceride and total cholesterol (Wieland, O. Methods of Enzymatic analysis. Bergermeyer, H. O., Ed., 1963. 211–214; Trinder, P. Ann Clin. Biochem. 1969. 6: 24–27). Measurement of plasma triglyceride, total cholesterol and HDL were done using commercial kits (D)r. Reddy's Diagnostic Division, Hyderabad, India).

| Compound | Dose (mg/kg) | Triglyceride (%)↓ |
| --- | --- | --- |
| Example 7 | 3 | 61 |
| Example 18 | 3 | 63 |
| Example 19 | 3 | 51 |

Formulae for calculation:

1. Percent reduction in Blood sugar/triglycerides/total cholesterol were calculated according to the formula:

$$\text{Percentage reduction } (\%) = \left[1 - \frac{TT/OT}{TC/OC}\right] \times 100$$

$OC$ = Zero day control group value $OT$ = Zero day treated group value $TC$ = Test day control group value $TT$ = Test day treated group value 2. LDL and VLDL cholesterol levels were calculated according to the formula:

$$\text{LDL cholesterol in mg/dl} = \left[\text{Total cholesterol} - \text{HDL cholesterol} - \frac{\text{triglyceride}}{5}\right] \text{mg/dl}$$

VLDL cholesterol in mg/dl=[Total cholesterol–HDL cholesterol–LDL cholesterol] mg/dl

What is claimed is:

1. An intermediate of formula (IIIm)

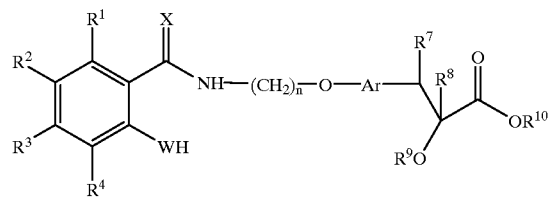

(IIIm)

where, X represents O or S; the groups $R^1$, $R^2$, $R^3$ and $R^4$ may be same or different and represent hydrogen, halogen, hydroxy, cyano, nitro, formyl; or unsubstituted or substituted groups selected from alkyl, cycloalkyl, alkoxy, cycloalkyloxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, aminoalkyl, hydroxyalkyl, alkoxyalkyl, aryloxyalkyl, aralkoxyalkyl, thioalkyl, alkylthio, alkoxycarbonylamino, aryloxycarbonylamino, aralkoxycarbonylamino, carboxylic acid or its amides, or sulfonic acid or its amides; W represents O; n is an integer ranging from 1–4; Ar represents an unsubstituted or substituted divalent aromatic or heterocyclic group; $R^7$ represents hydrogen atom, hydroxy, alkoxy, halogen, lower alkyl, or unsubstituted or substituted aralkyl group or forms a bond with $R^8$; $R^8$ represents hydrogen atom, hydroxy, alkoxy, halogen, lower alkyl, acyl group or unsubstituted or substituted aralkyl, or $R^8$ forms a bond together with $R^7$; $R^9$ represents hydrogen or unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminocarbonyl, acyl, heterocyclyl, heteroaryl, or heteroaralkyl groups; $R^{10}$ represents hydrogen or unsubstituted or substituted groups selected from alkyl, cycloalkyl, aryl, aralkyl, heterocyclyl, heteroaryl, or heteroaralkyl groups; and the linking group represented by —$(CH_2)_n$—O—may be attached either through nitrogen atom or carbon atom.

2. A process for the preparation of compound of formula (IIIm) as defined in claim 1, which comprises reacting a compound of formula (IVn)

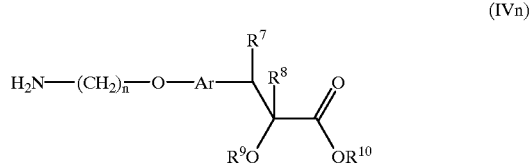

(IVn)

where all symbols are as defined earlier with a compound of formula (IVo) or (IVp)

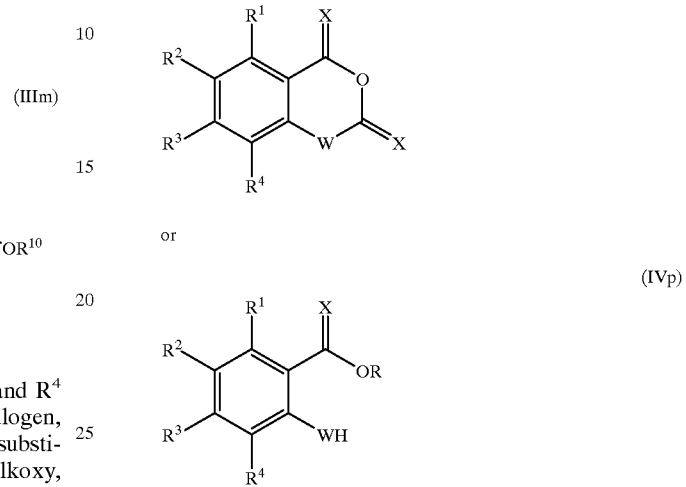

(IVo)

or (IVp)

where all symbols are as defined earlier.

3. An intermediate of formula (IVf)

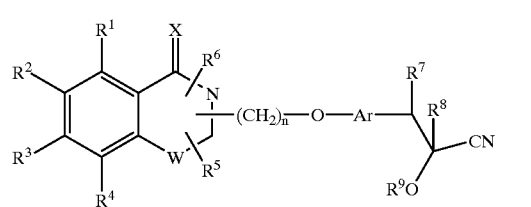

(IVf)

where X represents O or S; the groups $R^1$, $R^2$, $R^3$, $R^4$ and the groups $R^5$ and $R^6$ when attached to carbon atom may be the same or different and represent hydrogen, halogen, hydroxy, cyano, nitro, formyl; or unsubstituted or substituted groups selected from alkyl, cycloalkyl, alkoxy, cycloalkoxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, aminoalkyl, hydroxyalkyl, alkoxyalkyl, aryloxyalkyl, aralkoxyalkyl, thioalkyl, alkylthio, alkoxycarbonylamino, aryloxycarbonylamino, aralkoxycarbonylamino, carboxylic acid or its amides, or sulfonic acid or its amides; W represents O; n is an integer ranging from 1–4; Ar represents an unsubstituted or substituted divalent aromatic or heterocyclic group; $R^7$ represents hydrogen atom, hydroxy, alkoxy, halogen, lower alkyl, or unsubstituted or substituted aralkyl group or forms a bond with $R^8$; $R^8$ represents hydrogen atom, hydroxy, alkoxy, halogen, lower alkyl, acyl group or unsubstituted or substituted aralkyl or $R^8$ forms a bond together with $R^7$; $R^9$ represents hydrogen or unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminocarbonyl, acyl, heterocyclyl, heteroaryl, or heteroaralkyl groups; and the linking group represented by —(CH$_2$)$_n$—O—may be attached either through nitrogen atom or carbon atom.

4. A process for the preparation of compound of formula (IVf) defined above, where R$^7$ and R$^8$ represent hydrogen atoms and all other symbols are as defined above which comprises:

a) reacting a compound of formula (IIIa)

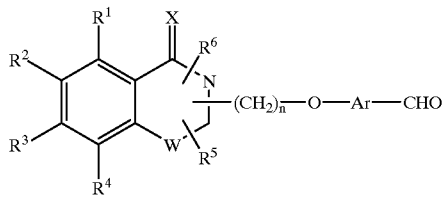

(IIIa)

where all symbols are as defined above with a compound of formula (IVi)

R$^9$OCH$_2$P$^+$PPh$_3$$^-$Hal  (IVi)

where R$^9$ represents unsubstituted or substituted groups selected from alkyl, cycloalkyl, aryl, aralkyl, alkoxyalkyl, aryloxyalkyl, alkoxycarbonyl, aryloxycarbonyl, alkylaminocarbonyl, arylaminocarbonyl, acyl, heterocyclyl, heteroaryl, or heteroaralkyl groups and Hal represents a halogen atom, to yield a compound of formula (IVj)

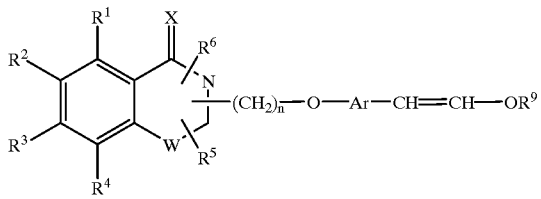

(IVj)

where all symbols are as defined above, b) reacting the compound of formula (IVj) with a compound of formula R$^9$OH where R$^9$ is as defined in part a to yield a, compound of formula (IVk),

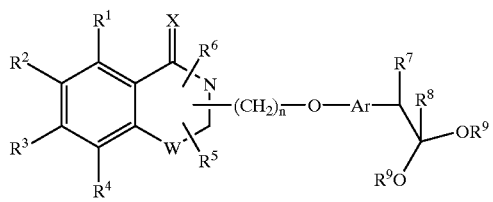

(IVk)

where all symbols are as defined above, and c) reacting a compound of formula (IVk) obtained above where all symbols are as defined above with trialkylsilyl cyanide to produce a compound of formula (IVf) where all symbols are as defined above.

5. An intermediate of formula (IVg)

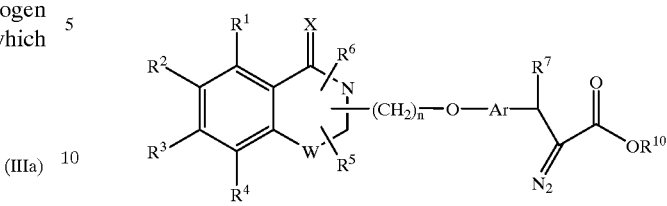

(IVg)

where X represents O or S; the groups R$^1$, R$^2$, R$^3$, R$^4$ and the groups R$^5$ and R$^6$ when attached to carbon atom may be the same or different and represent hydrogen, halogen, hydroxy, cyano, nitro, formyl; or unsubstituted or substituted groups selected from alkyl, cycloalkyl, alkoxy, cycloalkoxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamino which may be mono or dialkylamino group, arylamino, acylamino, aralkylamino, arinoalkyl, hydroxyalkyl, alkoxyalkyl, aryloxyalkyl, aralkoxyalkyl, thioalkyl, alkylthio, alkoxycarbonylamino, aryloxycarbonylamino, aralkoxycarbonylanino, carboxylic acid or its amides, or sulfonic acid or its amides; W represents O; n is an integer ranging from 1–4; Ar represents an unsubstituted or substituted divalent aromatic or heterocyclic group; R$^7$ represents hydrogen atom, hydroxy, alkoxy, halogen, lower alkyl, or unsubstituted or substituted aralkyl group; R$^{10}$ represents hydrogen or unsubstituted or substituted groups selected from alkyl, cycloalkyl, aryl, aralkyl, heterocyclyl, heteroaryl, or heteroaralkyl groups; and the linking group represented by —(CH$_2$)$_n$—O—may be attached either through nitrogen atom or carbon atom.

6. A process for the preparation of compound of formula (IVg)

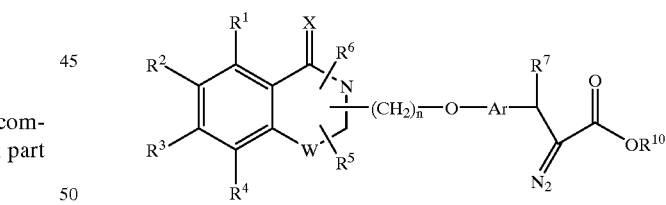

(IVg)

where X represents O or S; the groups R$^1$, R$^2$, R$^3$, R$^4$ and the groups R$^5$ and R$^6$ when attached to carbon atom may be the same or different and represent hydrogen, halogen, hydroxy, cyano, nitro, formyl; or unsubstituted or substituted groups selected from alkyl, cycloalkyl, alkoxy, cycloalkoxy, aryl, aryloxy, aralkyl, aralkoxy, heterocyclyl, heteroaryl, heteroaryloxy, heteroaralkyl, heteroaralkoxy, acyl, acyloxy, alkoxycarbonyl, aryloxycarbonyl, aralkoxycarbonyl, amino, alkylamnino which may be mono or dialkylamnino group, arylamino, acylamino, aralkylamino, aminoalkyl, hydroxyalkyl, alkoxyalkyl, aryloxyalkyl, aralkoxyalkyl, thioalkyl, alkylthio, alkoxycarbonylamino, aryloxycarbonylamino, aralkoxycarbonylamino, carboxylic acid or its amides, or sulfonic acid or its amides; W represents O; n is an integer ranging from 1–4; Ar represents an unsubstituted or substituted divalent aromatic or heterocyclic group; $R^7$ represents hydrogen atom, hydroxy, alkoxy, halogen, lower alkyl, or unsubstituted or substituted aralkyl group; $R^{10}$ represents hydrogen or unsubstituted or substituted groups selected from alkyl, cycloalkyl, aryl, aralkyl, heterocyclyl, heteroaryl, or heteroaralkyl groups; and the linking group represented by —$(CH_2)_n$—O— may be attached either through nitrogen atom or carbon atom, which comprises:

a) reacting a compound of formula (III)

(IIIe)

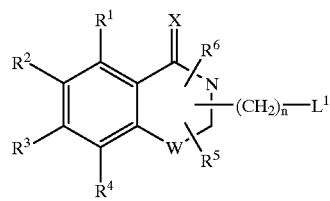

where $L^1$ is a leaving group and all other symbols are as defined above with a compound of formula (IVm)

(IVm)

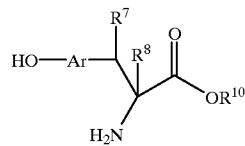

where $R^8$ is a hydrogen atom and all other symbols are as defined above, to yield a compound of formula (IVl)

(IVl)

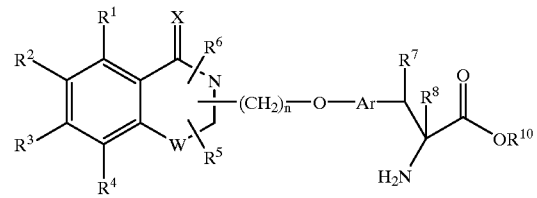

where $R^8$ is a hydrogen atom and all other symbols are as defined above, and reacting the compound of formula (IVl) obtained above with an appropriate diazotizing agent.

* * * * *